United States Patent
Mcallister et al.

(10) Patent No.: US 11,322,236 B1
(45) Date of Patent: May 3, 2022

(54) DATA ABSTRACTION SYSTEM ARCHITECTURE NOT REQUIRING INTEROPERABILITY BETWEEN DATA PROVIDERS

(71) Applicant: Precis, LLC, Sarasota, FL (US)

(72) Inventors: Jonathan M. Mcallister, Austin, TX (US); Neil R. Zamora, Sarasota, FL (US); Marjun Padrilanan Makinano, Sarasota, FL (US); Stephanie A. Kellogg, Austin, TX (US); Paul K. Davis, Sarasota, FL (US); Craiger J. Scheuer, Bradenton, FL (US)

(73) Assignee: PRECIS, LLC, Sarasota, FL (US)

( * ) Notice: Subject to any disclaimer, the term of this patent is extended or adjusted under 35 U.S.C. 154(b) by 199 days.

(21) Appl. No.: 16/926,149

(22) Filed: Jul. 10, 2020

Related U.S. Application Data

(63) Continuation-in-part of application No. 16/449,228, filed on Jun. 21, 2019.
(Continued)

(51) Int. Cl.
*G16H 10/60* (2018.01)
*G06F 16/2458* (2019.01)
*G06F 16/21* (2019.01)
*G06F 16/25* (2019.01)
*G06F 9/54* (2006.01)
(Continued)

(52) U.S. Cl.
CPC .............. *G16H 10/60* (2018.01); *G06F 9/547* (2013.01); *G06F 16/212* (2019.01); *G06F 16/2379* (2019.01); *G06F 16/2468* (2019.01); *G06F 16/258* (2019.01); *G06F 21/602* (2013.01); *H04L 63/08* (2013.01)

(58) Field of Classification Search
CPC ........ G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00
USPC ................................................ 705/3, 2, 20
See application file for complete search history.

(56) References Cited

U.S. PATENT DOCUMENTS 7,856,366 B2  12/2010 Dettinger et al.
8,423,382 B2   4/2013 Dettinger et al.
(Continued)

FOREIGN PATENT DOCUMENTS

CA          2637574 C     10/2017

OTHER PUBLICATIONS

A. Taherimonfared, T. W. Wlodarczyk and C. Rong, "Real-Time Handling of Network Monitoring Data Using a Data-Itensive Framework," 2013 IEEE 5th International Conference on Cloud Computing Technology and Science, Bristol, 2013, pp. 258-265, doi : 10.1109/CloudCom.2013.41.*
(Continued)

*Primary Examiner* — Robert W Morgan
*Assistant Examiner* — Charles P Coleman
(74) *Attorney, Agent, or Firm* — Wilson Sonsini Goodrich & Rosati

(57) ABSTRACT

Described are data abstraction systems, methods, and media for aggregating and abstracting data records from data providers, which are not substantially interoperable with each other. Features include data provider connector modules dynamically loaded, based on definitions stored on disk, that facilitate data mapping and individual matching.

30 Claims, 33 Drawing Sheets

Related U.S. Application Data

(60) Provisional application No. 62/828,928, filed on Apr. 3, 2019.

(51) Int. Cl.
    *G06F 21/60*     (2013.01)
    *G06F 16/23*     (2019.01)
    *H04L 29/06*     (2006.01)

(56) References Cited

U.S. PATENT DOCUMENTS

| | | | |
|---|---|---|---|
| 8,850,057 B2 | 9/2014 | Natoli et al. | |
| 2005/0049993 A1* | 3/2005 | Nori | G06F 16/284 |
| 2005/0050054 A1* | 3/2005 | Clark | G06F 16/25 |
| 2005/0262190 A1* | 11/2005 | Mamou | G06F 16/254 |
| | | | 709/203 |
| 2007/0078687 A1 | 4/2007 | Dettinger et al. | |
| 2009/0080408 A1* | 3/2009 | Natoli | H04L 67/327 |
| | | | 370/351 |
| 2010/0082732 A1 | 4/2010 | Guenther et al. | |
| 2010/0106684 A1 | 4/2010 | Pizzo et al. | |
| 2011/0040611 A1* | 2/2011 | Simmons | G06Q 30/0275 |
| | | | 705/14.41 |
| 2012/0215560 A1 | 8/2012 | Ofek et al. | |
| 2013/0132108 A1* | 5/2013 | Solilov | G16H 50/70 |
| | | | 705/2 |
| 2013/0173539 A1* | 7/2013 | Gilder | G06F 16/27 |
| | | | 707/622 |
| 2014/0095205 A1* | 4/2014 | Farooq | G16H 10/60 |
| | | | 705/3 |
| 2015/0006612 A1 | 1/2015 | Natoli et al. | |
| 2016/0063191 A1* | 3/2016 | Vesto | G06F 19/324 |
| | | | 705/2 |
| 2016/0092173 A1* | 3/2016 | Rodrigues | H04L 67/00 |
| | | | 717/106 |
| 2016/0197997 A1* | 7/2016 | Fossen | H04L 67/32 |
| | | | 709/219 |
| 2017/0032016 A1* | 2/2017 | Zinner | G06Q 10/063 |
| 2017/0039330 A1 | 2/2017 | Tanner, Jr. et al. | |
| 2017/0060537 A1* | 3/2017 | Mack | G06F 8/20 |
| 2017/0061338 A1* | 3/2017 | Mack | G06Q 10/067 |
| 2018/0260125 A1* | 9/2018 | Botes | G06F 3/067 |
| 2018/0293021 A1* | 10/2018 | Fossen | G06F 3/0655 |
| 2019/0034482 A1* | 1/2019 | Werner | G06F 16/211 |
| 2019/0172590 A1 | 6/2019 | Vesto et al. | |
| 2019/0294610 A1* | 9/2019 | Naidu | G06F 16/2448 |
| 2020/0250172 A1* | 8/2020 | Busjaeger | G06F 16/2365 |
| 2020/0264960 A1* | 8/2020 | Brooks | G06F 3/0604 |
| 2020/0314191 A1* | 10/2020 | Madhavan | H04L 67/16 |

OTHER PUBLICATIONS

Karlsson, Johan, and Oswaldo Trelles. "MAPI: a software framework for distributed biomedical applications." Journal of biomedical semantics vol. 4,1 4. Jan. 11, 2013, doi:10.1186/2041-1480-4-4.*

Glöckler, Falko et al. "The BioCASe Monitor Service—A tool for monitoring progress and quality of data provision through distributed data networks." Biodiversity data journal ,1 e968. Sep. 16, 2013, doi:10.3897/BDJ.1.e968.*

Dominic Duggan, "Enterprise Software Architecture and Design: Entities, Services, and Resources," IEEE, 2012.*

Karlsson et al., "MAPI: a software framework for distributed biomedical applications." Journal of biomedical semantics vol. 4,1 4. Jan. 11, 2013, doi:10.1186/2041-1480-4-4.*

Co-pending U.S. Appl. No. 16/449,228, filed Jun. 21, 2019.

U.S. Appl. No. 16/449,228 Office Action dated Feb. 12, 2020.

U.S. Appl. No. 16/449,228 Office Action dated Sep. 23, 2019.

* cited by examiner

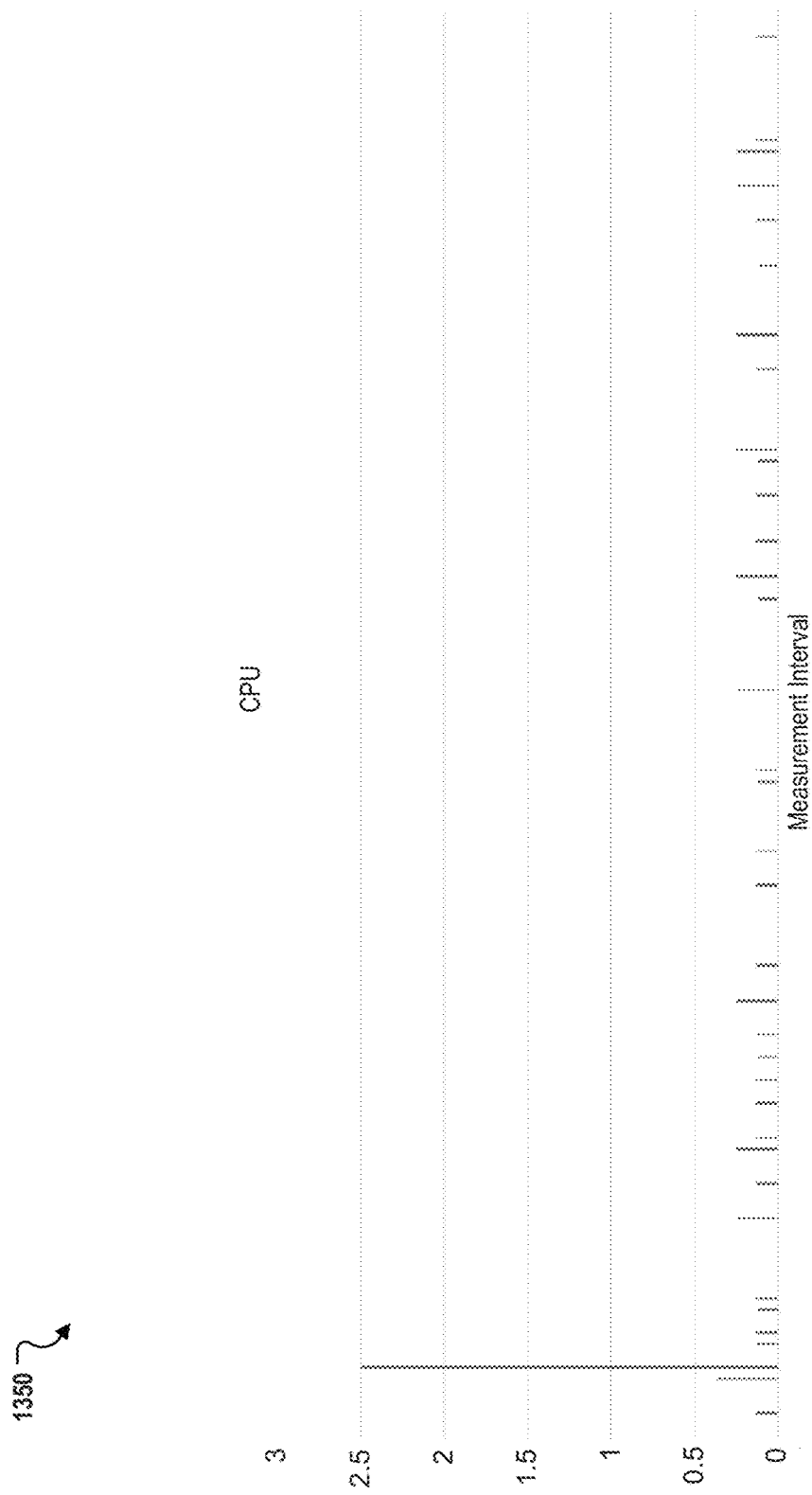

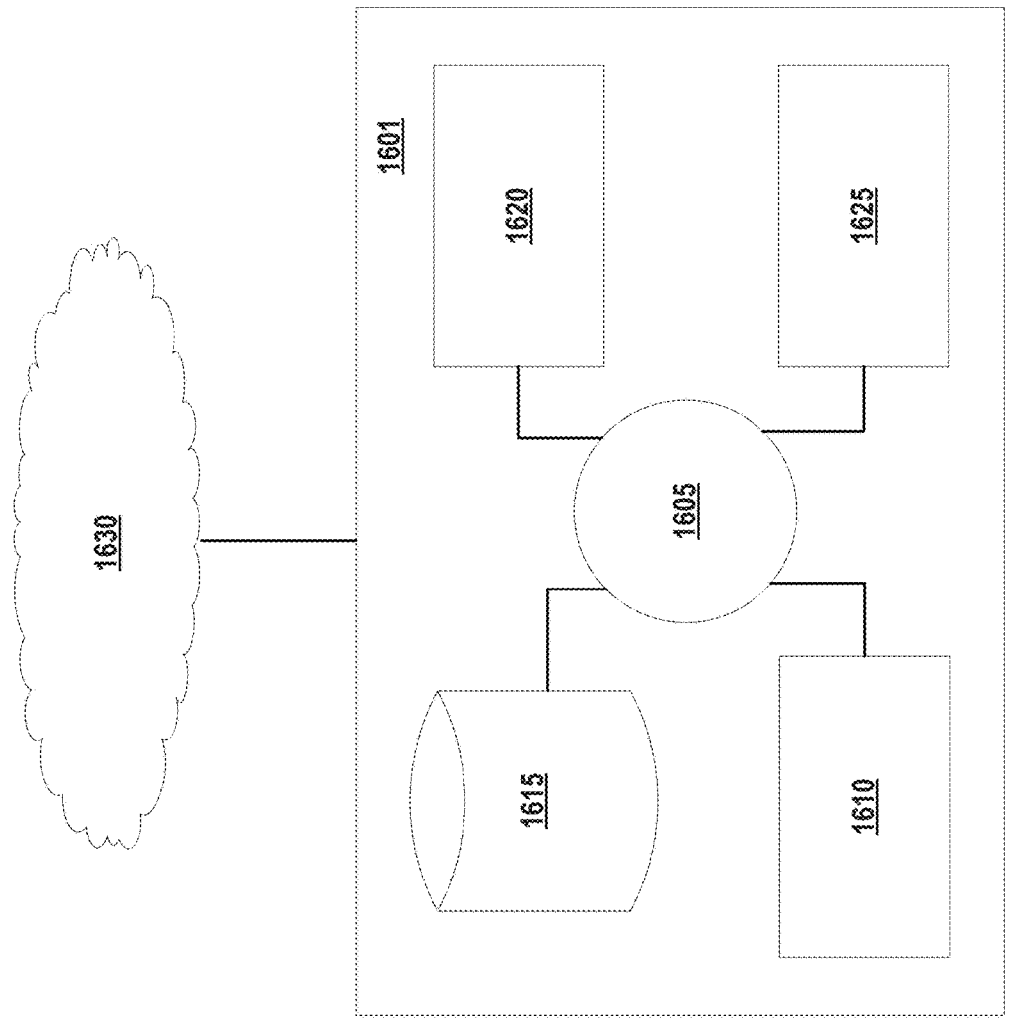
FIG. 16

DATA ABSTRACTION SYSTEM ARCHITECTURE NOT REQUIRING INTEROPERABILITY BETWEEN DATA PROVIDERS

CROSS-REFERENCE TO RELATED APPLICATIONS

This application is a Continuation-in-Part of U.S. application Ser. No. 16/449,228, filed Jun. 21, 2019, and claims the benefit of U.S. Provisional Application No. 62/828,928, filed Apr. 3, 2019, which application is incorporated in its entirety by reference.

BACKGROUND

Health information technology (HIT) involves the exchange of health information in an electronic environment. The Health Information Technology for Economic and Clinical Health (HITECH) Act was initiated under the (American Recovery and Reinvestment) ARRA Act. The act referenced the goal/need for interoperability. At the time, that goal was referred to, as the ability for disparate medical informatics systems to seamlessly communicate with each other. Empirical data coupled with hard data clearly illustrates that a decade later little if any progress has been achieved. Health Information Exchange (HIE's) have enjoyed some success but are limited in scope, often geographic in nature. Other attempts have involved the private sector creating micro-interoperability systems. Multiple schools of thought are attributed to this industry wide failure. Some believe that those in the electronic medical record (EMR) industry have intentionally thwarted attempts, i.e., data blocking. Fear of market share loss and exposure of proprietary information are just a few examples of this hypothesis. Some industry experts believe that the technology utilized with disparate systems created too many hurdles to fulfill this goal. These issues, along with other technological and business centric issues, are what have created this impasse. Additionally, when the reality that most all of the problem solvers tasked with this initiative are part of or embedded in the EMR industry is factored in, it is no small wonder that the net results are what they are.

SUMMARY

While HITECH was premised on the ability of systems to interoperate, and future regulations emphasized the need for health information exchange between providers, interoperability remains a distant goal. For while the EMRs were supposed to improve the delivery of health care, the reality is that they were designed and continue to be primarily used for billing purposes—not to track patients, symptoms, outcomes, and particularly not to provide longitudinal data of populations, something that is critical to truly understanding the extent of public health emergencies like Coronavirus Disease 2019 (COVID-19).

Moreover, the struggle to manage COVID-19 and reopen the economy—and keep it open—has been plagued by a lack of accurate data about the infection rate and deaths, as well as population-based information on patient biometrics, race and ethnicity, comorbidities, course of disease, treatments, and post-COVID course. Further, because our health system lacks the ability to aggregate accurate data from the disparate EMRs, billing databases, testing facilities, and other health care entities that collect patient information, officials, in many instances, are left blindly making life and death decisions and figuratively crossing their fingers hoping they are right. As such, the breadth of information that could improve decision making for not only the pandemic but all of health care is simply not available in an efficient, effective, or cohesive form. Thus, the most logical strategy is to develop a solution outside of the existing established technological and conceptual parameters.

Described herein, in certain embodiments, are data abstraction systems that provide a non-invasive way for EMR records to be consolidated into a comprehensive view of a patient's medical history by collecting data from different platforms/sources that can then be paired with artificial intelligence (AI) and analytics. The described data abstraction system integrates EMR vendors without requiring the EMR vendors to make changes to their data structures, install software, or modify existing systems. In some embodiments, the described abstraction system is Health Insurance Portability and Accountability Act (HIPAA) compliant and can connect to an EMR with scalability, customizable patient information, synchronization scheduling, data access at both the provider and patient level, applicability to multiple payor models, and data analytics to support fraud mitigation and cost management.

With over a decade of failed attempts by the medical informatics industry to interoperate or transmit medical information, the described data abstraction system can be employed to help providers reduce medical errors and enable patients to access key data elements of their medical record in one place. Moreover, the COVID-19 crisis crystallized another critical purpose for the described data abstraction system's unique architecture: the ability to pull data from the hundreds of thousands of disparate EMR systems to provide a clear picture of COVID-19 testing, diagnoses, emergency department visits, hospitalizations, complications, and deaths.

Employing the existing infrastructure provide by EMRs (e.g., through Health Level-7 (HL7), which includes a set of standards, formats and definitions for exchanging data and developing EMRs that was recently embellished with the federally mandated Fast Healthcare Interoperability Resources (FHIR) requiring an application programming interface (API)), the described data abstraction system provides a single source of medical truth for patients. However, one of the multiple barriers to interoperability is the reluctance of EMRs to share information when there is not a level playing field as highlighted by a 2015 report to Congress that found that many of these EMR companies engage in information blocking—knowingly and unreasonably interfering with the exchange or use of electronic health information. Even with financial penalties enacted in 2016 to discourage information blocking, the practice continues. Moreover, the volume of patient data is massive and is frequently updated. Thus, providing a system with the ability to both processes this data as quickly as possible while also integrating with existing systems, presents a monumental technical challenge.

For example, many data services use a "pass through"-like process to access data from origin systems and collate it for their users. As such, these origin systems must be operational for each request. Moreover, this process is not scaled per data endpoint. To solve these issues, in some embodiments, the described data abstraction system retrieves or is provided data from multiple sources and translates this data into a common format for storage. In some embodiments, to provide a more scalable solution, to this process a greater volume of data, the described system includes data provider connector modules that are assigned to a particular data source (e.g., an end point provider). In some embodiments, these modules are loaded based on a definition which are stored to disk. In some embodiments, once loaded, each data provider connector module employs an in-memory database to retrieve, process, and store received data (e.g., patient data). Such a solution provides for the increase in processing capacity required to adequately service the medical informatics industry. Once stored, the data may be updated on a customizable schedule, flagged, filtered, and re-served out. In some embodiments, the described data abstraction system employs a data store to persist the retrieved data. The use of such a data store results in increased accessibility for the translated data as the described data abstraction system is decoupled from the uptime of the origin services. Additionally, that data store remains available to internal or external sources in the collated form.

In some embodiments, the described data abstraction system provide access to real-time critical medical information from a single source, which eliminates the need to access multiple patient portals, request faxes, make phone calls, and send emails. In some embodiments, the described data abstraction system, allows consumers to control their medical information and support payors and providers in value-based care via intuitive dashboards that provide a centralized repository for the data required for success in population-based care.

In some embodiments, the design of the described data abstraction system fits cloud and big data concepts that make it scalable, easy to implement, and robust for analytic applications. In some embodiments, users can get alerts for special conditions, study pre-existing conditions, or ensure that proposed treatments are consistent with existing medications or allergies. In some embodiments, described data abstraction system provides local, state, and federal authorities, as well as health care professionals, with the valuable information they need to make data-driven decisions, decisions based on a single source of truth.

The described data abstraction system may be employed in industries where pass through is used. Such current usage industries include, for example, the travel industry (e.g., hotel booking, and flight booking). The described data abstraction system may be employed to broaden the scope of data applied to such databases systems as department of motor vehicles, homeland security, and commercial real estate. The described data abstraction system may be employed where little or no data is currently captured, for example, or a veterinary practice area. The described data abstraction system may be employed where no pre-existing business relationship or technical connection required. In some embodiments, the described data abstraction system requires no software to be installed at a data provider and provides unlimited scalability to meet national and international reporting needs. The described data abstraction system is also highly portable using iPhone operating system (iOS) and Android devices.

In one aspect, disclosed herein are data abstraction systems comprising: a data store comprising one or more data records, the data store defined according to a data format schema, the one or more data records comprising at least one Electronic Health Record (EHR); one or more processors; and a computer-readable storage device coupled to the one or more processors and having instructions stored thereon which, when executed by the one or more processors, cause the one or more processors to perform automated data abstraction operations comprising: dynamically loading a data provider connector module based on a definition of the data provider connector module retrieved from the computer-readable storage device and configured for a given data provider endpoint, the data provider connector module comprising: a sync scheduling definition, an accessor communication protocol client, a data translator module, and a data mapping system; receiving an instruction, in accordance with the sync scheduling definition, to request a data payload comprising one or more new or updated data records from the data provider endpoint over a network, the one or more new or updated data records defined according to a data records schema specified for the data provider endpoint; procuring, via the accessor communication protocol client, the data payload from the data provider endpoint over the network; processing, by the data translator module, the one or more new or updated data records by performing a set of automated mapping operations to map the data records schema to the data format schema; retrieving, by the data mapping system, one or more of the data records from the data store; assigning weighted values to a specified set of fields and attributes for each of the retrieved data records based on corresponding fields and attributes in the one or more new or updated data records; applying, by the data mapping system, an algorithm to evaluate a record match based on a calculated point value sum of the fields within the data record that match against a calculated match likelihood of N number of the matching fields; persisting the one or more new or updated data records to the data store; and making the one or more data records available via a standardized communication protocol or a user interface. In some embodiments, the data provider connector module is dynamically loaded through reflection or introspection of code. In some embodiments, the definition of the data provider connector module is retrieved from the computer-readable storage device without accessing or querying a database. In some embodiments, the data provider connector module further comprises a test connection method. In some embodiments, the accessor communication protocol client connects to the data provider endpoint after authenticating through an authentication service preconfigured at the data provider. In further embodiments, the definition of the data provider connector module comprises credentials, a Uniform Resource Identifier (URI), and an authentication protocol for the authentication service. In some embodiments, the definition of the data provider connector module further comprises custom automated instructions that define the communication protocol and automated mapping operations for the data provider connector module. In some embodiments, the automated mapping operations for the data records schema include custom fields defined by the data mapping system. In some embodiments, the one or more of the data records are retrieved from the data store based on fuzzy search logic. In some embodiments, the automated data abstraction operations further comprise, before persisting the updated data records, encrypting the updated data records. In some embodiments, the accessor communication protocol client procures the data payload from the data provider endpoint based on a specified technology standard, wherein the definition of the data provider connector module comprises a preferred communication protocol, and wherein the accessor communication protocol client processes the data records based on the preferred communication protocol. In some embodiments, the accessor communication protocol client supports communication protocol switching between a plurality of supported protocols. In a particular embodiment, the plurality of supported protocols comprises: FHIR, and Representational State Transfer (REST). In further embodiments, FHIR is used preferentially and a non-FHIR supported protocol is used where FHIR is not available at the data provider endpoint. In still further embodiments, the plurality of supported protocols is defined by the definition of the data provider connector module. In some embodiments, the instruction is received from a time-based job scheduler. In further embodiments, the instruction comprises a software-based trigger. In some embodiments, the automated data abstraction operations further comprise discarding at least one of the data records based on low measures of the weighted values assigned to the specified set of fields and attributes of the at least one of the data records. In some embodiments, the data abstraction is defined according to the definition of the data provider connector module. In some embodiments, the data provider connector module is implemented as a node allocated to the data provider endpoint. In further embodiments, the node is connected to a load balanced data store, and wherein the data store is replicated through a master/master replication system. In further embodiments, the node is provided though a horizontally scalable cloud architecture. In some embodiments, the system comprises a plurality of data provider connector modules dynamically loaded based on respective definitions retrieved from the computer-readable storage device, each of the definitions comprising: a sync scheduling definition, an accessor communication protocol client, a data translator module, and a data mapping system. In various further embodiments, each of the data provider connector modules is hosted at a distinct server, server cluster, cloud node, or cloud architecture. In some embodiments, the system further comprises a user device, the user device comprising a client instantiated thereon, the client comprising the user interface, wherein the user interface is provided at least one of the data records via a FHIR communication protocol implemented API. In further embodiments, a last sync time and a device identifier associated with the user device is persisted for the user interface by the API. In some embodiments, the one or more data records are made available via FHIR coupled with a standardized API. In various embodiments, the data provider endpoint and the data provider connector module support one or more of: HL7, International Classification of Diseases 10 (ICD-10), and FHIR. In some embodiments, the at least one EHR comprises at least one EMR. In some embodiments, the one or more new or updated data records comprise at least one new or updated EHR. In further embodiments, the at least one new or updated EHR comprises at least one new or updated EMR. In some embodiments, the data abstraction is defined for the data provider endpoint such that the data provider endpoint does not interoperate with other data provider endpoints registered with the data abstraction system. In some embodiments, the data store comprises an in-memory database.

In another aspect, disclosed herein are computer-implemented data abstraction methods comprising: maintaining a data store comprising one or more data records, the data store defined according to a data format schema, the one or more data records comprising at least one EHR; dynamically loading a data provider connector module based on a definition of the data provider connector module retrieved from a computer-readable storage device of the computer and configured for a given data provider endpoint, the data provider connector module comprising: a sync scheduling definition, an accessor communication protocol client, a data translator module, and a data mapping system; receiving an instruction, in accordance with the sync scheduling definition, to request a data payload comprising one or more new or updated data records from the data provider endpoint over a network, the one or more new or updated data records defined according to a data records schema specified for the data provider endpoint; procuring, via the accessor communication protocol client, the data payload from the data provider endpoint over the network; processing, by the data translator module, the one or more new or updated data records by performing a set of automated mapping operations to map the data records schema to the data format schema; retrieving, by the data mapping system, one or more of the data records from the data store; assigning weighted values to a specified set of fields and attributes for each of the retrieved data records based on corresponding fields and attributes in the one or more new or updated data records; applying, by the data mapping system, an algorithm to evaluate a record match based on a calculated point value sum of the fields within the data record that match against a calculated match likelihood of N number of the matching fields; persisting the one or more new or updated data records to the data store; and making the one or more data records available via a standardized communication protocol or a user interface. In some embodiments, the data provider connector module is dynamically loaded through reflection or introspection of code. In some embodiments, the definition of the data provider connector module is retrieved from the computer-readable storage device without accessing or querying a database. In some embodiments, the data provider connector module further comprises a test connection method. In some embodiments, the accessor communication protocol client connects to the data provider endpoint after authenticating through an authentication service preconfigured at the data provider. In further embodiments, the definition of the data provider connector module comprises credentials, a URI, and an authentication protocol for the authentication service. In some embodiments, the definition of the data provider connector module further comprises custom automated instructions that define the communication protocol and automated mapping operations for the data provider connector module. In some embodiments, the automated mapping operations for the data records schema include custom fields defined by the data mapping system. In some embodiments, the one or more of the data records are retrieved from the data store based on fuzzy search logic. In some embodiments, the method further comprises, before persisting the updated data records, encrypting the updated data records. In some embodiments, the accessor communication protocol client procures the data payload from the data provider endpoint based on a specified technology standard, wherein the definition of the data provider connector module comprises a preferred communication protocol, and wherein the accessor communication protocol client processes the data records based on the preferred communication protocol. In some embodiments, the accessor communication protocol client supports communication protocol switching between a plurality of supported protocols. In a particular embodiment, the plurality of supported protocols comprises: FHIR, and REST. In further embodiments, FHIR is used preferentially and a non-FHIR supported protocol is used where FHIR is not available at the data provider endpoint. In further embodiments, the plurality of supported protocols is defined by the definition of the data provider connector module. In some embodiments, the instruction is received from a time-based job scheduler. In further embodiments, the instruction comprises a software-based trigger. In some embodiments, the method further comprises discarding at least one of the data records based on low measures of the weighted values assigned to the specified set of fields and attributes of the at least one of the data records. In some embodiments, the data abstraction is defined according to the definition of the data provider connector module. In some embodiments, the data provider connector module is implemented as a node allocated to the data provider endpoint. In further embodiments, the node is connected to a load balanced data store, and wherein the data store is replicated through a master/master replication system. In further embodiments, the node is provided though a horizontally scalable cloud architecture. In some embodiments, the method comprises dynamically loading a plurality of data provider connector modules based on respective definitions retrieved from the computer-readable storage device, each of the definitions comprising: a sync scheduling definition, an accessor communication protocol client, a data translator module, and a data mapping system. In various further embodiments, wherein each of the data provider connector modules is hosted at a distinct server, server cluster, cloud node, or cloud architecture. In some embodiments, the method further comprises providing, to a user device, a client to be instantiated on the user device, the client comprising the user interface, and providing at least one of the data records to the client via a FHIR communication protocol implemented API for display at the user interface. In further embodiments, the method further comprises persisting, by the API and for the user interface, a last sync time and a device identifier associated with the user device. In some embodiments, the one or more data records are made available via FHIR coupled with a standardized API. In various embodiments, the data provider endpoint and the data provider connector module support one or more of: HL7, ICD-10, and FHIR. In some embodiments, the at least one EHR comprises at least one EMR. In some embodiments, the one or more new or updated data records comprise at least one new or updated EHR. In further embodiments, the at least one new or updated EHR comprises at least one new or updated EMR. In some embodiments, the data abstraction is defined for the data provider endpoint such that the data provider endpoint does not interoperate with other data provider endpoints registered with the data abstraction system. In some embodiments, the data store comprises an in-memory database.

In another aspect, disclosed herein are non-transitory computer-readable storage media encoded with a computer program including instructions executable by one or more processors to perform automated data abstraction operations comprising: maintaining a data store comprising one or more data records, the data store defined according to a data format schema, the one or more data records comprising at least one EHR; dynamically loading a data provider connector module based on a definition of the data provider connector module retrieved from the computer-readable storage media and configured for a given data provider endpoint, the data provider connector module comprising: a sync scheduling definition, an accessor communication protocol client, a data translator module, and a data mapping system; receiving an instruction, in accordance with the sync scheduling definition, to request a data payload comprising one or more new or updated data records from the data provider endpoint over a network, the one or more new or updated data records defined according to a data records schema specified for the data provider endpoint; procuring, via the accessor communication protocol client, the data payload from the data provider endpoint over the network; processing, by the data translator module, the one or more new or updated data records by performing a set of automated mapping operations to map the data records schema to the data format schema; retrieving, by the data mapping system, one or more of the data records from the data store; assigning weighted values to a specified set of fields and attributes for each of the retrieved data records based on corresponding fields and attributes in the one or more new or updated data records; applying, by the data mapping system, an algorithm to evaluate a record match based on a calculated point value sum of the fields within the data record that match against a calculated match likelihood of N number of the matching fields; persisting the one or more new or updated data records to the data store; and making the one or more data records available via a standardized communication protocol or a user interface. In some embodiments, the data provider connector module is dynamically loaded through reflection or introspection of code. In some embodiments, the definition of the data provider connector module is retrieved from the computer-readable storage media without accessing or querying a database. In some embodiments, the data provider connector module further comprises a test connection method. In some embodiments, the accessor communication protocol client connects to the data provider endpoint after authenticating through an authentication service preconfigured at the data provider. In further embodiments, the definition of the data provider connector module comprises credentials, a URI, and an authentication protocol for the authentication service. In some embodiments, the definition of the data provider connector module further comprises custom automated instructions that define the communication protocol and automated mapping operations for the data provider connector module. In some embodiments, the automated mapping operations for the data records schema include custom fields defined by the data mapping system. In some embodiments, the one or more of the data records are retrieved from the data store based on fuzzy search logic. In some embodiments, the automated data abstraction operations further comprise, before persisting the updated data records, encrypting the updated data records. In some embodiments, the accessor communication protocol client procures the data payload from the data provider endpoint based on a specified technology standard, wherein the definition of the data provider connector module comprises a preferred communication protocol, and wherein the accessor communication protocol client processes the data records based on the preferred communication protocol. In some embodiments, the accessor communication protocol client supports communication protocol switching between a plurality of supported protocols. In a particular embodiment, the plurality of supported protocols comprises: FHIR, and REST. In further embodiments, FHIR is used preferentially and a non-FHIR supported protocol is used where FHIR is not available at the data provider endpoint. In further embodiments, the plurality of supported protocols is defined by the definition of the data provider connector module. In some embodiments, the instruction is received from a time-based job scheduler. In further embodiments, the instruction comprises a software-based trigger. In some embodiments, the automated data abstraction operations further comprise discarding at least one of the data records based on low measures of the weighted values assigned to the specified set of fields and attributes of the at least one of the data records. In some embodiments, the data abstraction is defined according to the definition of the data provider connector module. In some embodiments, the data provider connector module is implemented as a node allocated to the data provider endpoint. In further embodiments, the node is connected to a load balanced data store, and wherein the data store is replicated through a master/master replication system. In further embodiments, the node is provided though a horizontally scalable cloud architecture. In some embodiments, the automated data abstraction operations further comprise dynamically loading a plurality of data provider connector modules based on respective definitions retrieved from the computer-readable storage media, each of the definitions comprising: a sync scheduling definition, an accessor communication protocol client, a data translator module, and a data mapping system. In various further embodiments, each of the data provider connector modules is hosted at a distinct server, server cluster, cloud node, or cloud architecture. In some embodiments, the one or more data records are made available via FHIR coupled with a standardized API. In various embodiments, the data provider endpoint and the data provider connector module support one or more of: HL7, ICD-10, and FHIR. In some embodiments, the at least one EHR comprises at least one EMR. In some embodiments, the one or more new or updated data records comprise at least one new or updated EHR. In further embodiments, the at least one new or updated EHR comprises at least one new or updated EMR. In some embodiments, the data abstraction is defined for the data provider endpoint such that the data provider endpoint does not interoperate with other data provider endpoints registered with the data abstraction system. In some embodiments, the data store comprises an in-memory database.

It is appreciated that methods in accordance with the present disclosure can include any combination of the aspects and features described herein. That is, methods in accordance with the present disclosure are not limited to the combinations of aspects and features specifically described herein, but also may include any combination of the aspects and features provided.

The details of one or more embodiments of the present disclosure are set forth in the accompanying drawings and the description below. Other features and advantages of the present disclosure will be apparent from the description and drawings, and from the claims.

BRIEF DESCRIPTION OF THE DRAWINGS

A better understanding of the features and advantages of the present subject matter will be obtained by reference to the following detailed description that sets forth illustrative embodiments and the accompanying drawings of which:

FIGS. 13A-13G depict various graphs that include measurements of example benchmarking data;

FIGS. 14A-14G depict various non-limiting exemplary pages of an administrative portal provided to user devices by the described data abstraction system;

FIG. 16 depicts a non-limiting exemplary processing device.

DETAILED DESCRIPTION

Figure 1:
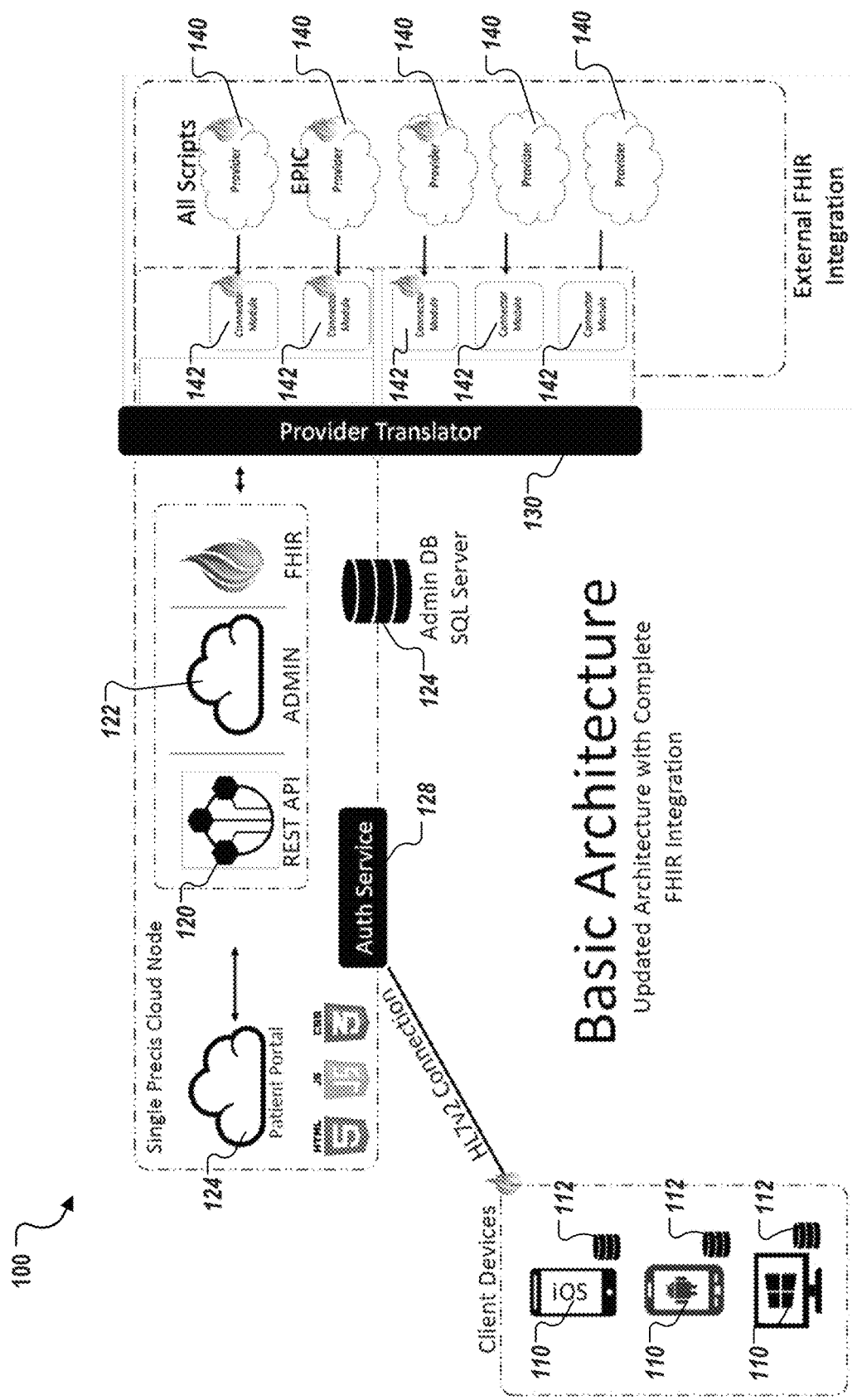
FIG. 1 depicts a non-limiting exemplary architecture that may be employed to provide the described data abstraction system.

Described herein, in certain embodiments, are data abstraction systems comprising: a data store comprising one or more data records, the data store defined according to a data format schema, the one or more data records comprising at least one EHR; one or more processors; and a computer-readable storage device coupled to the one or more processors and having instructions stored thereon which, when executed by the one or more processors, cause the one or more processors to perform automated data abstraction operations comprising: retrieving a definition of a data provider connector module from the computer-readable storage device without accessing or querying a database; dynamically loading the data provider connector module based on the definition, the data provider connector module configured for a data provider endpoint, wherein the data provider endpoint does not interoperate with other data provider endpoints registered with the data abstraction system, the data provider connector module comprising: a sync scheduling definition, an accessor communication protocol client, a data translator module, and a data mapping system; receiving an instruction, in accordance with the sync scheduling definition, to request a data payload comprising one or more new or updated data records from the data provider endpoint over a network, the one or more new or updated data records defined according to a data records schema specified for the data provider endpoint; procuring, via the accessor communication protocol client, the data payload from the data provider endpoint over the network, wherein the accessor communication protocol client supports communication protocol switching among a plurality of supported protocols, wherein the definition of the data provider connector module comprises a preferred communication protocol, and wherein the accessor communication protocol client processes the data records based on the preferred communication protocol; processing, by the data translator module, the one or more new or updated data records by performing a set of automated mapping operations to map the data records schema to the data format schema; retrieving, by the data mapping system, one or more of the data records from the data store; assigning weighted values to a specified set of fields and attributes for each of the retrieved data records according to the mapped schemas and based on values for corresponding fields and attributes in the one or more new or updated data records; applying, by the data mapping system, an algorithm to evaluate a record match based on a calculated point value sum of the fields within the data record that match against a calculated match likelihood of N number of the matching fields; persisting the one or more new or updated data records to the data store; and making the one or more data records available via a standardized communication protocol or a user interface.

Also described herein, in certain embodiments, are computer-implemented data abstraction methods comprising: maintaining a data store comprising one or more data records, the data store defined according to a data format schema, the one or more data records comprising at least one EHR; retrieving a definition of a data provider connector module from the computer-readable storage device without accessing or querying a database; dynamically loading the data provider connector module based on the definition, the data provider connector module configured for a data provider endpoint, wherein the data provider endpoint does not interoperate with other data provider endpoints registered with the data abstraction system, the data provider connector module comprising: a sync scheduling definition, an accessor communication protocol client, a data translator module, and a data mapping system; receiving an instruction, in accordance with the sync scheduling definition, to request a data payload comprising one or more new or updated data records from the data provider endpoint over a network, the one or more new or updated data records defined according to a data records schema specified for the data provider endpoint; procuring, via the accessor communication protocol client, the data payload from the data provider endpoint over the network, wherein the accessor communication protocol client supports communication protocol switching among a plurality of supported protocols, wherein the definition of the data provider connector module comprises a preferred communication protocol, and wherein the accessor communication protocol client processes the data records based on the preferred communication protocol; processing, by the data translator module, the one or more new or updated data records by performing a set of automated mapping operations to map the data records schema to the data format schema; retrieving, by the data mapping system, one or more of the data records from the data store; assigning weighted values to a specified set of fields and attributes for each of the retrieved data records according to the mapped schemas and based on values for corresponding fields and attributes in the one or more new or updated data records; applying, by the data mapping system, an algorithm to evaluate a record match based on a calculated point value sum of the fields within the data record that match against a calculated match likelihood of N number of the matching fields; persisting the one or more new or updated data records to the data store; and making the one or more data records available via a standardized communication protocol or a user interface.

Also described herein, in certain embodiments, are non-transitory computer-readable storage media encoded with a computer program including instructions executable by one or more processors to perform automated data abstraction operations comprising: maintaining a data store comprising one or more data records, the data store defined according to a data format schema, the one or more data records comprising at least one EHR; retrieving a definition of a data provider connector module from the computer-readable storage device without accessing or querying a database; dynamically loading the data provider connector module based on the definition, the data provider connector module configured for a data provider endpoint, wherein the data provider endpoint does not interoperate with other data provider endpoints registered with the data abstraction system, the data provider connector module comprising: a sync scheduling definition, an accessor communication protocol client, a data translator module, and a data mapping system; receiving an instruction, in accordance with the sync scheduling definition, to request a data payload comprising one or more new or updated data records from the data provider endpoint over a network, the one or more new or updated data records defined according to a data records schema specified for the data provider endpoint; procuring, via the accessor communication protocol client, the data payload from the data provider endpoint over the network, wherein the accessor communication protocol client supports communication protocol switching among a plurality of supported protocols, wherein the definition of the data provider connector module comprises a preferred communication protocol, and wherein the accessor communication protocol client processes the data records based on the preferred communication protocol; processing, by the data translator module, the one or more new or updated data records by performing a set of automated mapping operations to map the data records schema to the data format schema; retrieving, by the data mapping system, one or more of the data records from the data store; assigning weighted values to a specified set of fields and attributes for each of the retrieved data records according to the mapped schemas and based on values for corresponding fields and attributes in the one or more new or updated data records; applying, by the data mapping system, an algorithm to evaluate a record match based on a calculated point value sum of the fields within the data record that match against a calculated match likelihood of N number of the matching fields; persisting the one or more new or updated data records to the data store; and making the one or more data records available via a standardized communication protocol or a user interface.

Certain Definitions

Unless otherwise defined, all technical terms used herein have the same meaning as commonly understood by one of ordinary skill in the art to which the present subject matter belongs. As used in this specification and the appended claims, the singular forms "a," "an," and "the" include plural references unless the context clearly dictates otherwise. Any reference to "or" herein is intended to encompass "and/or" unless otherwise stated.

As used herein, the term "real-time" refers to transmitting or processing data without intentional delay given the processing limitations of a system, the time required to accurately obtain data and images, and the rate of change of the data and images. In some examples, "real-time" is used to describe the presentation of information obtained from components of embodiments of the present disclosure.

EMRs include digital version of patients' charts and include a patient's medical history, diagnoses and treatments by a particular physician, nurse practitioner, specialist, dentist, surgeon or clinic. EHRs are also digital version of patients' charts, but it is a more inclusive snapshot of a patient's medical history that may be shared among multiple facilities and agencies. Both EHRs and EMRs allow clinicians to track data over time, easily identify when patients are due for preventive screenings or checkups, check how patients are doing on certain parameters (e.g., blood pressure readings), and monitor and improve overall quality of care.

Generally, an in-memory database is a type of purpose-built database that relies primarily on memory for data storage, in contrast to databases that store data on disk or solid state drives (SSDs). In-memory databases are designed to attain minimal response time by eliminating the need to access disks. Because all data is stored and managed exclusively in main memory, it is at risk of being lost upon a process or server failure. In-memory databases can persist data on disks by storing each operation in a log or by taking snapshots.

As used herein, the term "interoperability" includes the ability for various HIT (e.g., the API's provided by an EMR vendor) to exchange, interpret and use data cohesively, and to work together within and across organizational boundaries in order to advance the effective delivery of healthcare for individuals and communities. According to Healthcare Information and Management Systems Society, Inc. (HIMSS), purposes of health data exchange architectures, application interfaces and standards include enabling data to be accessed and shared appropriately and securely across the complete spectrum of care, within all applicable settings and with relevant stakeholders, including by the individual. HIMSS defines the first three levels of interoperability as: 1) Foundational, 2) Structural, and 3) Semantic. Where the Sematic level provides for common underlying models and codification of the data including the use of data elements with standardized definitions from publicly available value sets and coding vocabularies, providing shared understanding and meaning to the user. However, as described above, current health/patient data providing systems (e.g., EMR providers) are siloed solutions and thus form a siloed healthcare ecosystem, which does not achieve the defined Semantic level of interoperability. The described system bridges this gap to provide a more Semantic like level healthcare ecosystem by integrating existing data provider systems, without requiring interoperability among these provider systems.

Overview

The integration of patient records into a single source of truth that is made available to patients would, among other benefits, improve the quality of health care, prevent medical errors, reduce health care costs, increase administrative efficiencies, decrease paperwork, and expand access to affordable health care. However, it is imperative that the privacy and security of EMRs be ensured as this information is maintained and transmitted electronically. Moreover, data exchange schema and standards should permit data to be shared across clinician, lab, hospital, pharmacy, and patient regardless of the application or application vendor. However, as described above, the various solutions available in HIT are developed in silos, leading to inoperable and disjointed communications when integrated. Providing a solution for these technical problems by employing specific technical implementations, the described data abstraction system abstracts and connects to multiple data source providers via a network connection and retrieves one or many informational resources from the defined data sources. The system connects to these providers via a defined industry protocol. The informational resources once retrieved are then collated and amalgamated into a unified format and stored in encrypted form in the network attached database system. The described system's architecture provides both the speed and scalability necessary to process such large, complex, and frequently updated volumes of data (e.g., from EMR providers) without requiring interoperability among the providers of such data. Thus, allowing the large number of data providers flexibility in the implementations of their APIs, while providing a technical solution for the standardization of the data shared among them through secure channels that protect patient privacy. The described system provides this technical solution for the integration of HIT during the complexity of global pandemics and other health crises with lives on the line.

FIG. 1 depicts an example architecture 100 that may be employed to provide the described data abstraction system. As depicted, the example architecture 100 includes software clients 110, client database 112, REST API 120, administrative portal 122, administrative database 124, patient portal 124, authentication service 128, provider translator module 130, data provider endpoints 140, and data provider connector modules 142. In some embodiments, the described data abstraction system provided through the example architecture 100 is HL7v2 compliant. Health Level-7 or HL7v2 refers to a set of international standards for transfer of clinical and administrative data between software applications used by various healthcare providers. In some embodiments, the described data abstraction system provided through the example architecture 100 leverages international ICD-10 standards to support international use. In some embodiments, the patient portal 124 includes a web access point that allows users (e.g., patients) to log in and view their information.

In some embodiments, the example architecture 100 is employed to retrieve one or many informational resources (e.g., patient records) from the defined data provider endpoints 140. The informational resources may include, for example, EHR/EMR. Exemplary data providers include, by way of non-limiting examples: Allscripts, Cerner, Epic, McKesson, Athena Health, eClinicalWorks, GE Healthcare, Greenway Health, Meditech, NextGen (Quality Systems, Inc.), and the like.

In some embodiments, the data provider connector modules 142 are employed to synchronize data received from the data provider endpoints 140 and provide a common communication translation service, through the provider translator module 130, between the REST API 120 and the providers 140. For example, the data provider connector modules 142 may perform web request calls to retrieve Personal Health Information (PHI) from a specific provider and send the retrieved data to the translator module 130. The data provider connector modules 142 may also act as a bridge between the described data abstraction system and PHI data providers. Such data access allows the providers to procure and distribute, for example, individual disparate medical data to the client software via the client sync and administrative capabilities provide by the example architecture 100. For example, the data provider connector modules 142 may connect, through a network, to a respective data provider endpoint 140 via, for example, a defined industry protocol(s). Each of the data provider connector modules 142 then retrieves the respective informational resources from the respective data provider endpoint 140. In some embodiments, the retrieved informational resources are then collated and amalgamated into a unified format and stored in encrypted form in the administrative database 124. In some embodiments, the example architecture 100 is a cloud-based administration solution providing periodic (e.g., daily) synchronization of data provided by the data provider endpoints 140. For example, each data provider connector module 142 retrieves personal EHR/EMR records from a respective data provider endpoint 140 periodically based on a definition provided by the respective data provider. The retrieved data is then stored in the administration database 124. In some embodiments, such a data sync is one directional (e.g., import only). In some embodiments, the data provider connector modules 142 are implemented as modular solution that allows for additional connectors to be developed and connected to the described data abstraction system.

In some embodiments, to ensure each data provider connector modules 142 individually maps data retrieved from a given data provider a connector definition will have a mapping file (e.g., a JavaScript Object Notation (JSON) file) that pre-determines corresponding fields from the data records in the administrative data base 124. In some embodiments, the data provider connector modules 142 are dynamically loaded through reflection or introspection of code. In some embodiments, the data provider connector modules 142 are dynamically loaded based on respective definitions retrieved from disk to provide a more scalable solution and thus the ability to processes more data (see FIGS. 12A-12D). In some embodiments, each of the definitions includes a sync scheduling definition, an accessor communication protocol client, a data translator module, and a data mapping system.

In some embodiments, the data provider connector modules 142 are implemented as a node allocated to the respective data provider endpoint 140. For example, such a node may be connected to a load balanced data store that replicated through a master/master replication system. In some embodiments, a node is provided though a horizontally scalable cloud architecture.

In some embodiments, the data provider connector modules 142 employ an in memory database to store and retrieve patient data. Such a solution provides for an increase in overall system throughput (e.g., processing speed) and allows for the receiving and processing of more patient data from the data end points.

In some embodiments, each of the data provider connector modules 142 have the option to leverage FHIR; however, when FHIR is not available on the data providers end, the connector module has the option to leverage various web standard protocols (e.g., and Simple Object Access Protocol (SOAP), REST, and so forth). In some embodiments, this is automatically switched on when FHIR is disabled for a given data provider connector modules 142. In some embodiments, the specific definition of the protocol is defined within the code specified for that connector module.

In some embodiments, the provider translator module 130 acts as translators for the described data abstraction system. For example, the provider translator module 130 interprets the data retrieved from a respective data provider endpoint 140 by each of the respective data provider connector modules 142, and maps the retrieved data to the records persisted to the administration database 124. In some embodiments, the provider translator module 130 converts the retrieved data into a common format that can be sent to the software clients 110. In some embodiments, to ensure proper entity data record mapping, the provider translator module 130 determines the potentiality for a record match based on an algorithm that assigns a weighted value to X number of fields, while performing an algorithmic fuzzy match search within the administration database 124. In some embodiments, upon finding a likely match, the provider translator module 130 performs a threshold analysis of the match based on predefined values within the system. In some embodiments, the data provider connector modules 142 is employed to enforce enabling and disabling of the connector modules set by the administrator. In some embodiments, the provider translator module 130 is embedded within a data provider connector module 142 based on the definition provided by the data providers.

The software clients 110 include client implementations supporting systems, such as Windows®, iOS, Android®. Each software client includes a respective client database 112.

In some embodiments, to ensure HIPAA security compliance, the example architecture 100 includes encryption and decryption logic. The administrative portal 122 provides granular controls over the encryption functionality. In some embodiments, such logic provides the ability to define (at a field level) which specific data should be made secret. In some embodiments, data is stored at rest within the administrative database 124 in an encrypted form, and all data transmitted over any network is also encrypted in transit, based on the configured encryption and decryption logic. Data in transit, or data in motion, is data actively moving from one location to another, such as across the internet or through a private network. Data protection in transit is the protection of this data while it is traveling from network to network or being transferred from a local storage device to a cloud storage device, such as described above within the example architecture 100. Data at rest is data that is not actively moving from device to device or network to network, such as data stored on a hard drive, laptop, flash drive, or archived/stored in some other way (e.g., within the administrative database 124).

In some embodiments, within the example architecture 100, encryption and decryption interfaces represent a translation service that ensures data that is stored and transferred between the various components is encrypted and decrypted effectively. To ensure proper compliance with HL7v2 and HIPAA.

In some embodiments, encryption and decryption interfaces provide a final translation layer between the administrative portal 122 and the data provider connector modules 142, the data provider connector modules 142 and the respective data provider endpoints 140, the administrative portal 122 and the administer database 124, the software clients 110 and the administrative portal 122, and the software clients 110 and the respective local client databases 112. The administrative portal is described in more detail below in the description of FIGS. 14A-14G, which depict example pages of an administrative portal.

To alleviate over congestion of networks, and long waited queue times; the example architecture 100 provides a set of custom sync definitions that may be unique to each data provider. In some embodiments, the example architecture 100 employs the administrators to specify acute timings and execution scheduling for automated data requests; for information from a given data provider in CRON format. For example, each schedule for the data provider connector module's 142 may be defined on disk and may report to a master scheduling system, which adheres to and executes the defined sync schedule per provider.

In some embodiments, the authentication service 128 is employed to control access from the software clients 110 into the described data abstraction system. For example, the authentication service 128 is employed to ensure that only authorized personnel have appropriate access to the data stored on the client database 112.

In addition to pre-defined access roles, biometric authentication for the patient access may also be implemented through the authentication service 128. Biometric access control has been leveraged in multiple software solutions in recent history and typically relies on device users (fingerprint) to enforce such access controls. Currently Biometric access controls are available for iOS devices (e.g., iPhone, iPad, etc.) and android [phones]. The example architecture 100 may include a single access point to the entire system thus allowing patients, doctors, nurses, and other healthcare personnel with access to the patient information portal on the client software.

In some embodiments, the authentication service 128 provides restrictions based on roles, which is more commonly known as role based security. Defined user roles provided through the authentication service 128 may include 1) administrator/provider and healthcare worker/patient. In some embodiments, the administrator/provider role is filled by the provider and administration personnel for the provider. In some embodiments, the healthcare worker/patient role is filled by EMTs, Physicians, Nurses, and related healthcare workers.

The example architecture 100 includes numerous ways to visibly display or output the stored data records. For example, the software clients 110 may include a web browser application that displays a UI that accesses the REST API 120. In some embodiments, the REST API 120 is implemented using RESTful architecture and includes: 1) REST API+JSON data formatting; 2) Encrypted data and secure authentication adhering to HL7 standards; and 3) a user interface (UI)/user experience (UX) that leverages the REST API 120 for its operability. Moreover, the REST API 120 also provides API access through a uniquely tailored FHIR server, which can be further leveraged to provide patient data to the software clients 110 via a custom application installed on the devices. In addition to the FHIR Client devices, the example architecture 100 provides a client web-based portal to provide end user access to their specific data stored within the system. In some embodiments, a UI provides two specific access regimes: 1) administration user access, and 2) patient or end user data access.

In some embodiments, the software clients 110 provide healthcare personnel with at-a-glance insights into a patient's current medical health, history, and related relevant information. In some embodiments, the software clients 110 provide healthcare personnel with access to accurate PHI while treating a patient. In some embodiments, updates to patient information come from the provider/connectors after such information has been updated on their end.

In some embodiments, a UI and UX of the software clients 110 adheres to a color palette. In some embodiments, the user interface will include of multiple screens (see FIGS. 14A-14G and 15A-15D) including, by way of non-limiting examples, the following: 1) login/access screen; 2) patient and provider primary view screen (read-only mode); 3) directives/donor list screen; 4) directive/donor information; 5) health report screen (with print capabilities); 6) physician list screen; 7) physician contact details screen; 8) emergency contact information screen; 9) Surgery history list screen; 10) medical conditions screen; 11) medical flags screen; 12) known allergies screen; 13) medications listing; and 14) medical event list.

Figure 2:
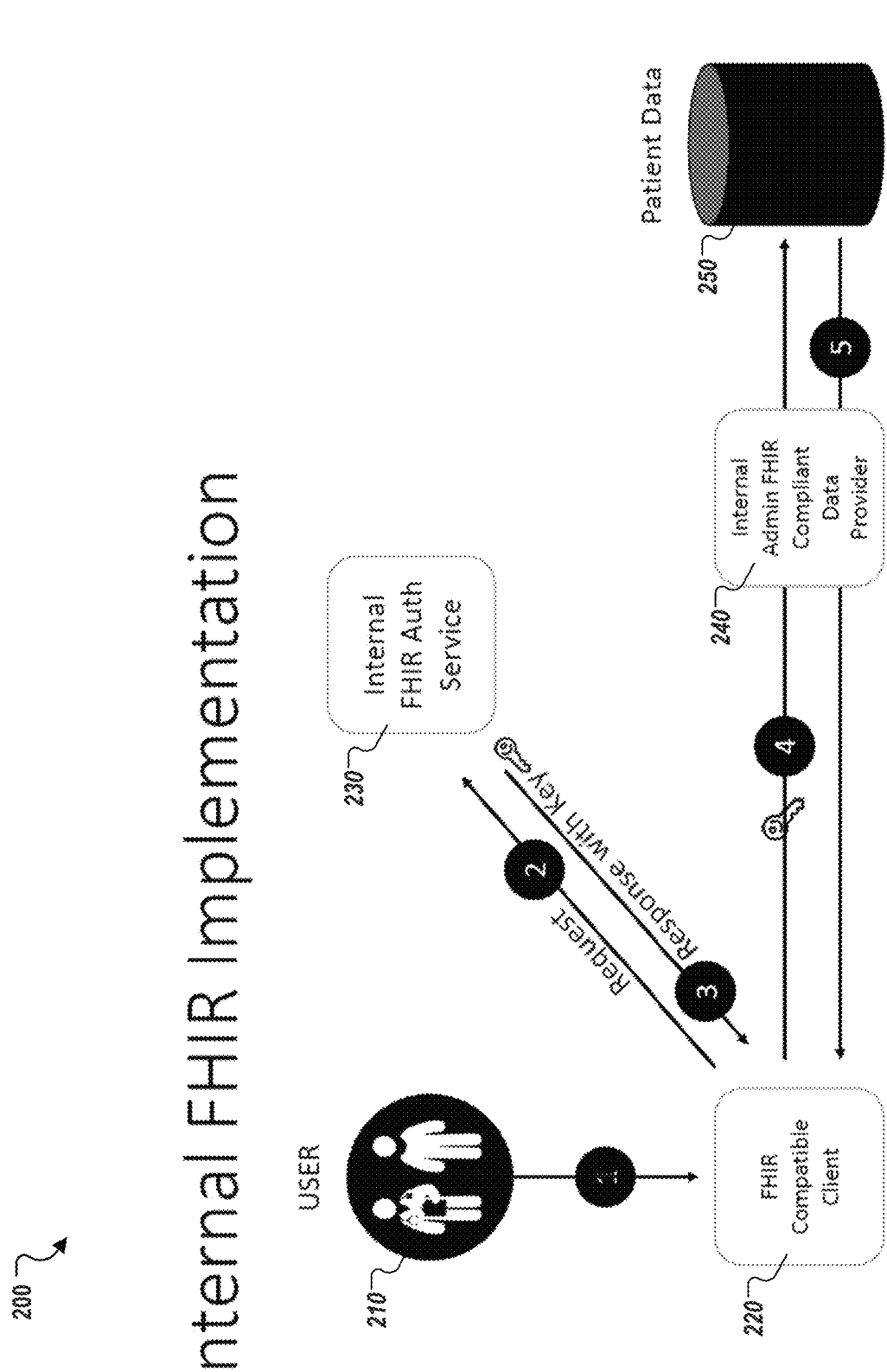
FIG. 2 depicts a non-limiting exemplary internal FHIR implementation deployed through the example architecture.

FIG. 2 depicts an example internal FHIR implementation 200 deployed through the example architecture 100. The example internal FHIR implementation 200 includes users 210, a FHIR compatible client 220, an internal FHIR Authentication service 230, administrative FHIR compliant data provider 240, and patient database 250. In some embodiments, the FHIR compatible client 210 is a software client, such as software clients 110 of FIG. 1, that is compatible with FHIR. In some embodiments, the internal FHIR Authentication service 230 is provided via the REST API 120 of FIG. 1. In some embodiments, the administrative FHIR compliant data provider 240 includes a data provider endpoint, such as data provider endpoints 140 of FIG. 1, that provides access to the patient data stored to the patient database 250.

As depicted, the user 210 accesses (1) the FHIR compatible client 220 deployed to a client device. The FHIR compatible client 220 provides (2) a request for access to the internal FHIR Authentication service 230, which provides (3) a response that includes a key. The FHIR compatible client 220 provides (4) the key to the administrative FHIR compliant data provider 240 for access (5) to the patient database 250.

Figure 3:
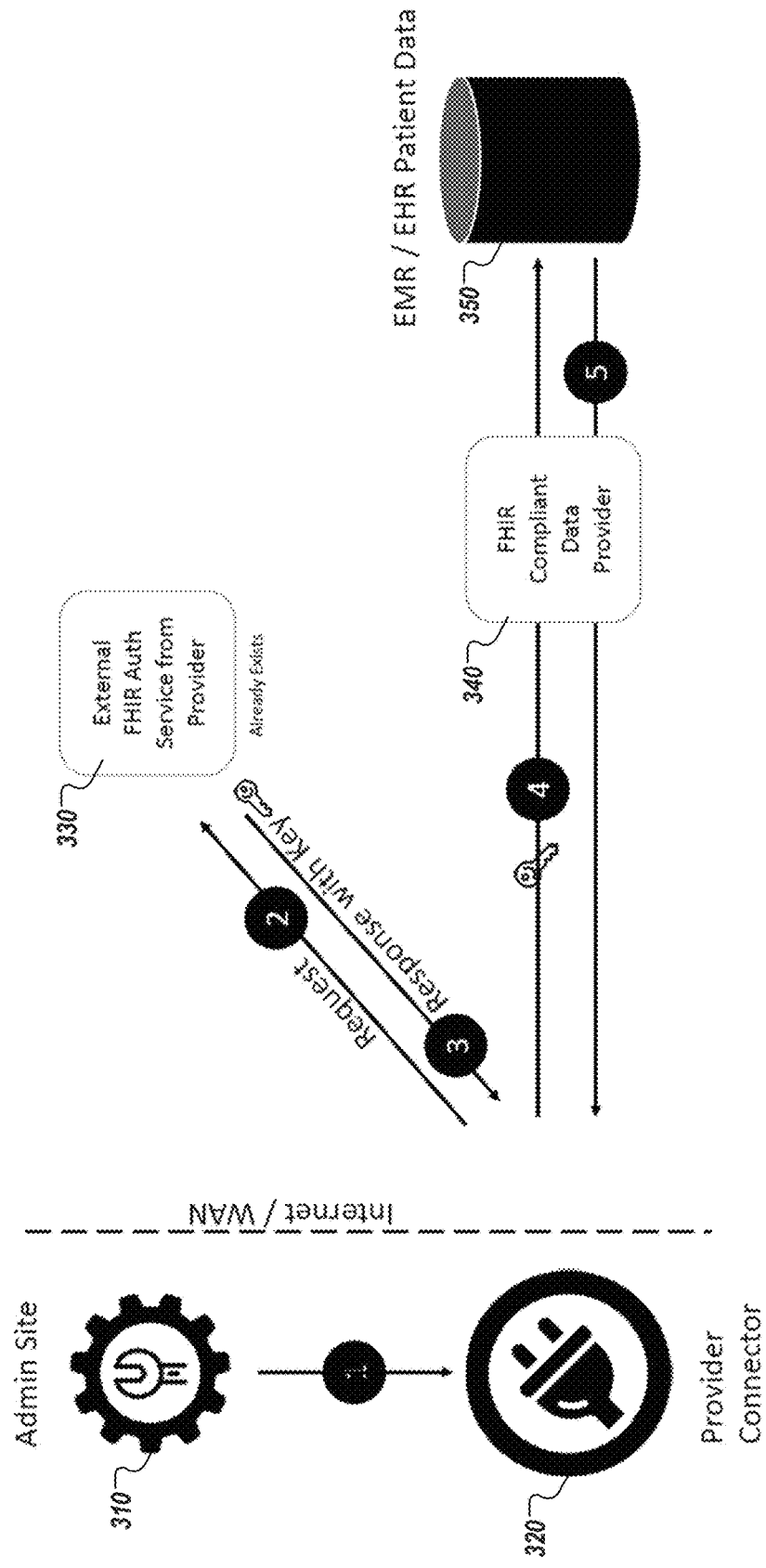
FIG. 3 depicts a non-limiting exemplary external FHIR implementation deployed through the example architecture.

FIG. 3 depicts an example external FHIR implementation 300 deployed through the example architecture 100. The example external FHIR implementation 300 includes an administrator site 310, a provider connector 320, an external FHIR Authentication service 330, a FHIR compliant data provider 340, and an EMR/EHR patient database 350. In some embodiments, the administrator site 310 provides authentication from the connector module 142 to the respective provider 140.

As depicted, the administrator site 310 accesses (1) the provider connector 320. The provider connector 320 provides (2) a request for access to the external FHIR Authentication service 330, which provides (3) a response that includes a key. The provider connector 320 provides (4) the key to the FHIR compliant data provider 340 for access (5) to an EMR/EHR patient database 350.

Figure 4:
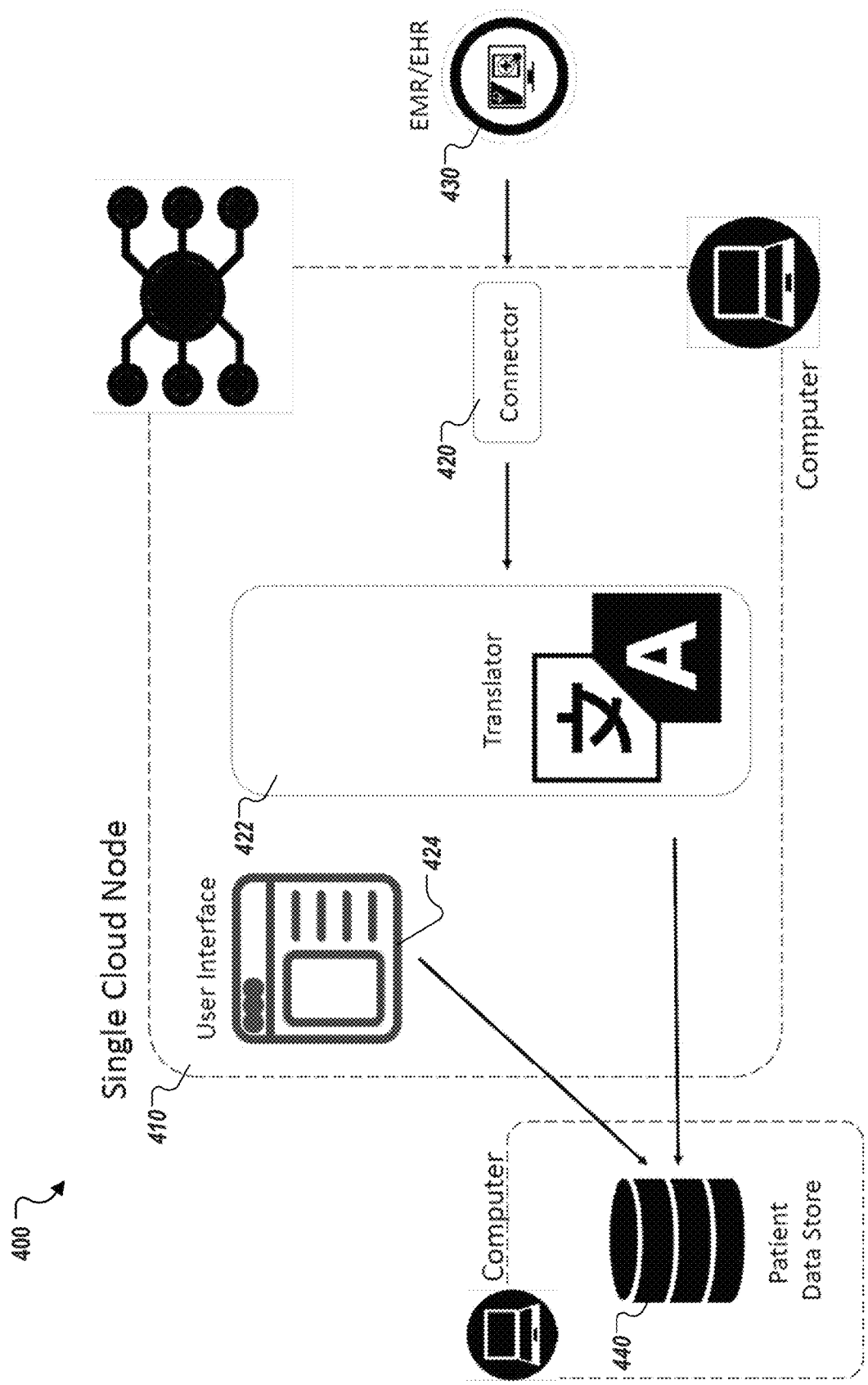
FIG. 4 depicts a non-limiting exemplary implementation of a single cloud node.

FIG. 4 depicts an example implementation 400 of a single cloud node 410. The single cloud node 410 may be employed within the described data abstraction system as a data provider connector module, such as the data provider connector module 142 of FIG. 1. The example implementation 400 includes patient data store 440, which is substantially similar to the administrative database 124 of FIG. 1, and the data provider end point 430, which is substantially similar to the data provider endpoints 140 of FIG. 1.

As depicted, the single cloud node 410 includes a connector module 420, a translator module 422, and an administrative UI 424. The connector module 420 is employed to retrieve data records from the data provider end point 430 as described above. The translator module 422 maps the records retrieved from the data provider end point 430 to the data format schema of the patient data store 440, according to a respective definition file, such as described above with regard to the provider translator module 130 of FIG. 1. In some embodiments, such a definition file provides for a mapping a custom fields between the schemas. The administrative UI 424 accesses the mapped records stored in the patient data store 440 and provides the information to, for example, software clients 110 of FIG. 1.

Figure 5:
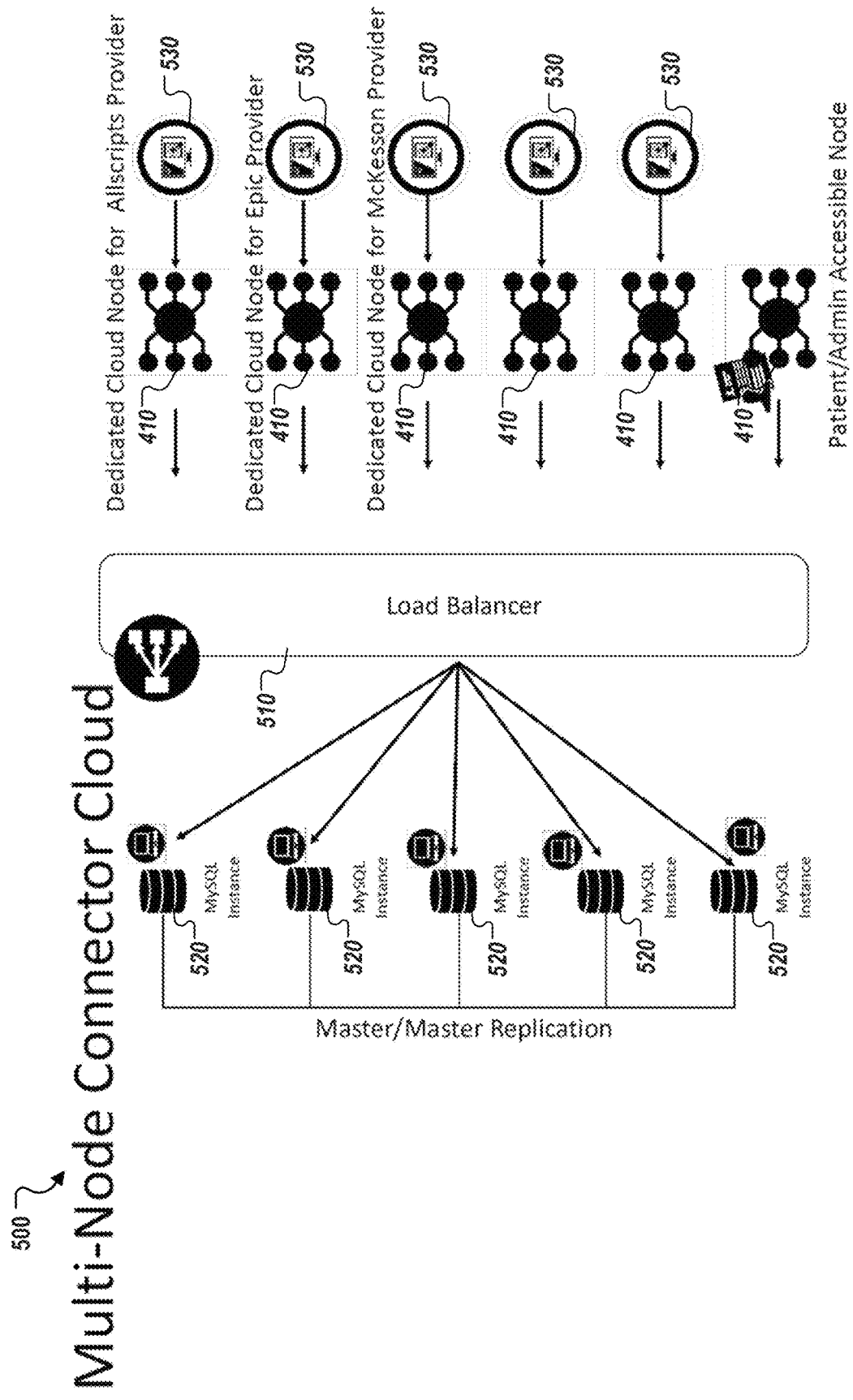
FIG. 5 depicts a non-limiting exemplary multi-node connector cloud implementation that may be employed for load balancing allowing for scalability of the described data abstraction system.

FIG. 5 depicts an example of a multi-node connector cloud implementation 500 that may be employed for load balancing allowing for scalability of the described data abstraction system. The depicted implementation 500 includes single cloud nodes 410, which are allocated to respective data provider end points 530. In some embodiments, the cloud nodes 410 connect to the database instances 520, which are replicated through master/master replication. In some embodiments, the database instances 520 are load balanced through a load balancer 510. In some embodiments, a load balancer is a piece of hardware (or virtual hardware) that acts like a reverse proxy to distribute network or application traffic across different servers. In some embodiments, the load balancer 510 is employed with the described system to improve the concurrent capacity and overall reliability of the database instances 520.

Figure 6:
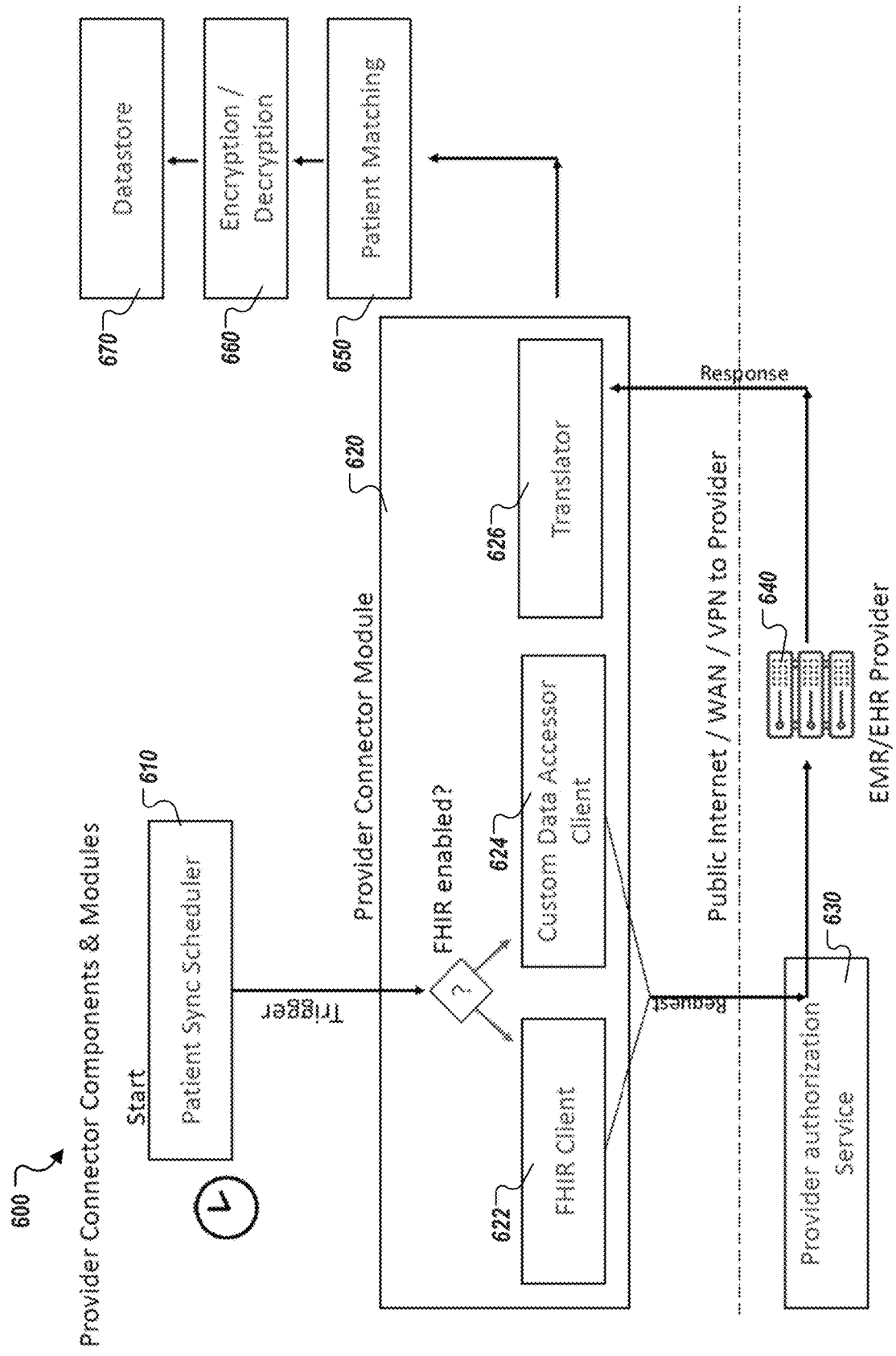
FIG. 6 depicts a non-limiting exemplary implementation of provider connector components and modules that are employed to retrieve records from a respective provider endpoint.

FIG. 6 depicts an implementation 600 of provider connector components and modules that are employed to retrieve records from a respective provider endpoint. The depicted implementation 600, includes patient synchronization scheduler 610; provider connector module 620, which is substantially similar to data provider connector modules 142 of FIG. 1; provider authentication service 630, records provider 640; patient matching module 650, encryption/decryption module 660, and data store 670 which is substantially similar to administrative database 124 of FIG. 1.

The patient synchronization scheduler 610 triggers activation of the connector module 620 to retrieve records from the records provider 640. In some embodiments, the patient synchronization scheduler 610 is a CRON based scheduler. One activated, the provider connector module 610 determines whether the client is implemented as a FHIR client 622 or a custom data accessor client 624. In some embodiments, the active client connects, via the provider authentication service 630, to the records provider 640 to retrieve any added or updated data records. In some embodiments, retrieved records are processed by the translator module 626 according to the mapping definitions provided by the records provider 640. The translator model determines the potentiality for a record match based on an algorithm that assigns a weighted value to X number of fields, while performing an algorithmic fuzzy match search within the data store 670. In some embodiments, once the retrieved records are translated, the patient matching model matches the translated data to patient records within the data store 670. In some embodiments, the mapped records are encrypted in the data store 670. In such embodiments, the encryption/decryption module 660 encrypts data stored to the data store 670 and decrypts data received from the data store 670.

Figure 7:
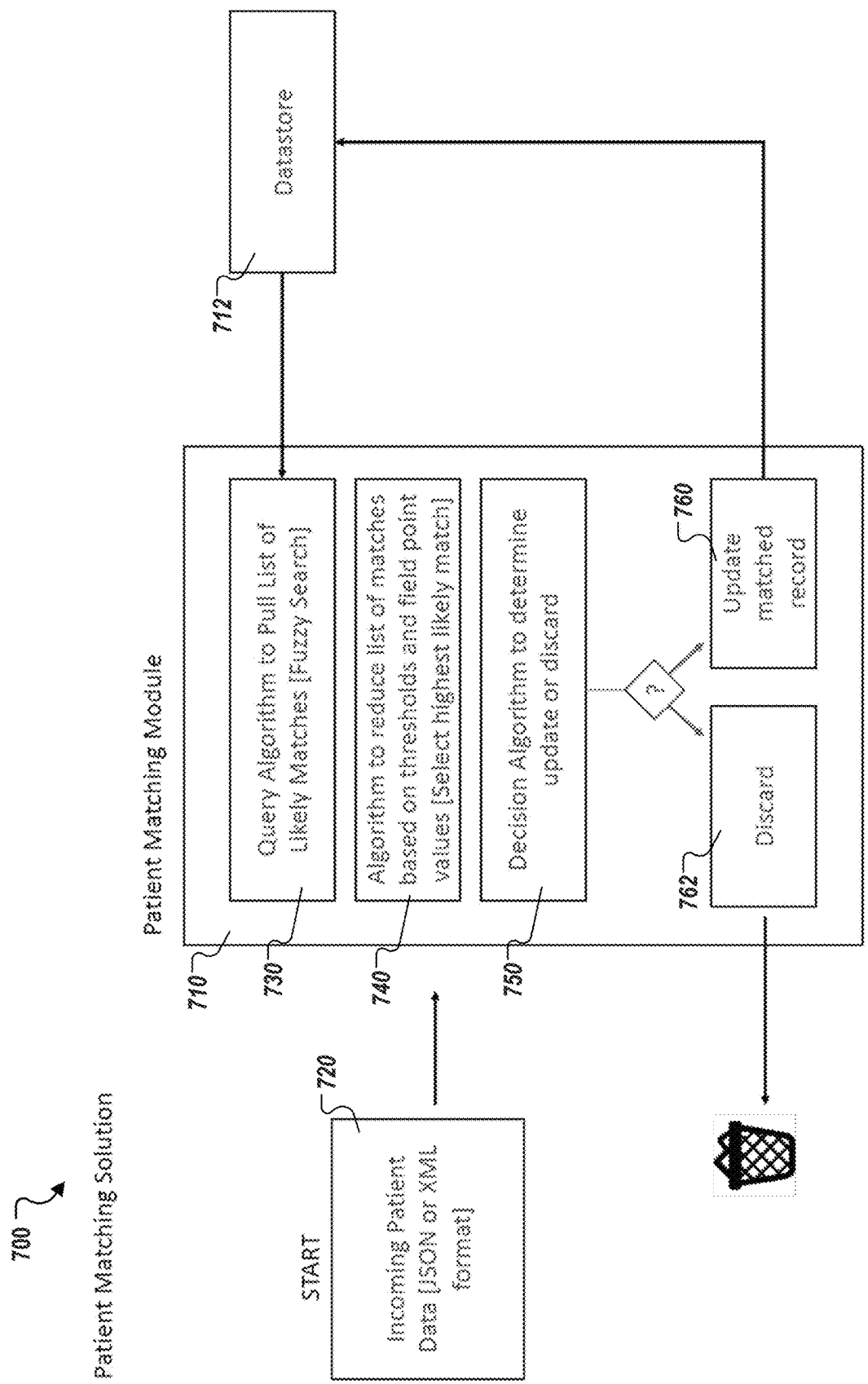
FIG. 7 depicts a non-limiting exemplary process implemented with a matching module.

FIG. 7 depicts an example process 700 implemented with a matching module 710. In some embodiments, the matching module 710 is a component of a translator module, such as the translator module 130 of FIG. 1. At 720, record data, such a patient data, is received from, for example, a provider connector module, such as the data provider connector modules 142 of FIG. 1. At 730, a query algorithm, such a fuzzy search, is performed on the data store 712 to pull a list of likely matches for the received records data. At 740, an algorithm to reduce the list of matches is performed. Is some embodiments, the algorithm is based on thresholds and field point values where the highest likely matches are retained in the list. At 750, a decision algorithm is performed to determine whether to update 760 the remaining matched record(s) from the data store 712 with the received record data or to discard 762 the received record data. For example, the decision algorithm may be based on the threshold and field point values from step 1140. At 760, the received records are discarded based on the decision algorithm. At 762, the matched records are updated with the received records data and persisted to the data store 712.

Figure 8:
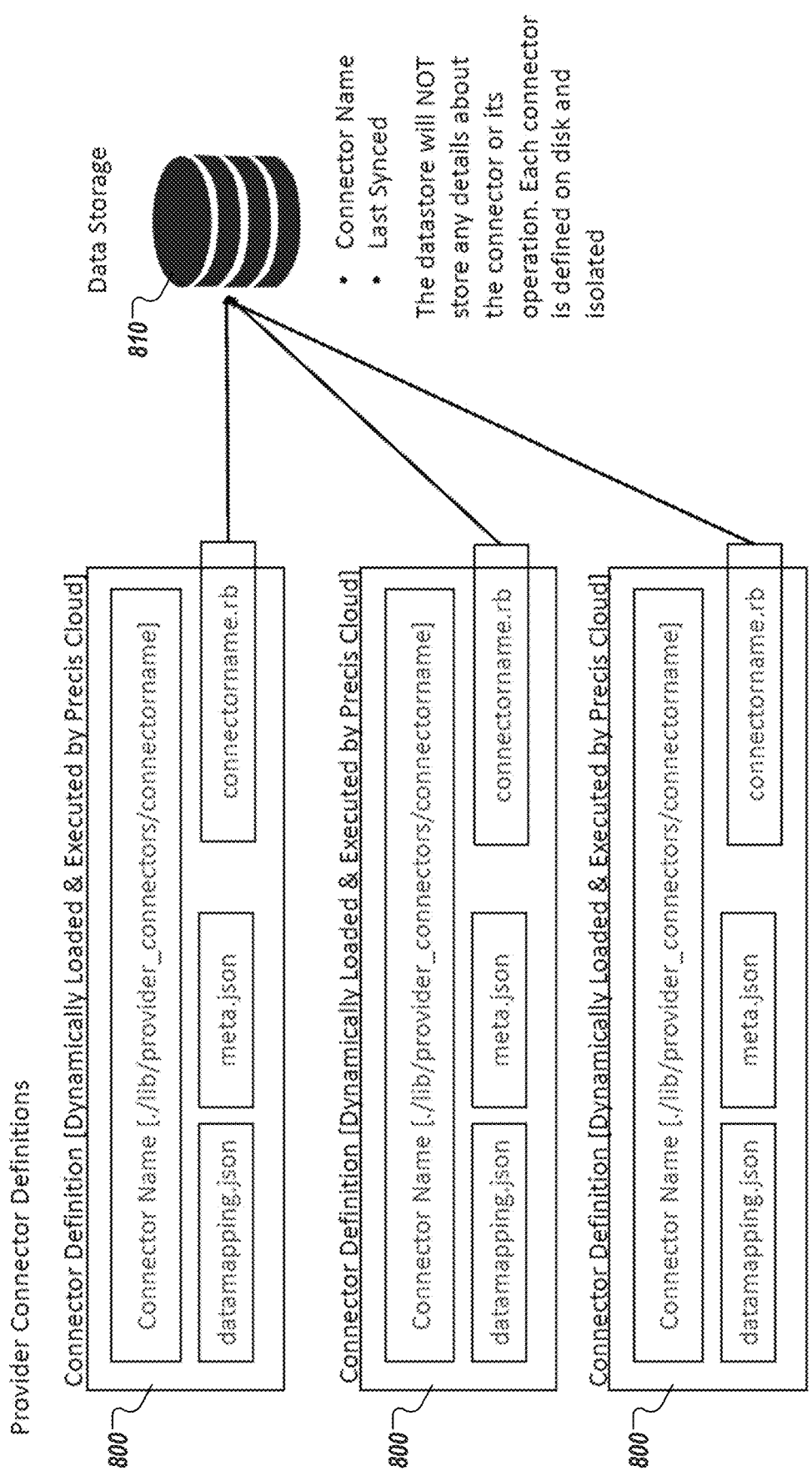
FIG. 8 depicts a non-limiting exemplary provider connector definitions and a data store.

FIG. 8 depicts example provider connector definitions 800 and data store 810. In some embodiments, the data store 810 substantially similar to the administrative database 124 of FIG. 1. In some embodiments, the provider connector definitions 800 are defined on disk and isolated. In some embodiments, once retrieved from disk, the definitions 800 are executed by the described data abstraction system to dynamically load respective data provider connector modules, such as data provider connector modules 142 of FIG. 1, which are employed to retrieved data records from respective provider endpoint. In some embodiments, the retrieved data records are used to update records in the data store 810. In some embodiments, the provider connector definitions 800 define a name for a connector within the described data abstraction system; a mapping between a data format schema employed within the data store 810 and a data records schema specified for a respective data provider from which the loaded connector module retrieved data records; definitions for metadata regarding, for example, the data records retrieved from the respective data provider; and credentials and location information to establish a connection to the data store 810. In some embodiments, the data store 810 does not store any details about the connector modules or the operation of the connector modules.

Figure 9:
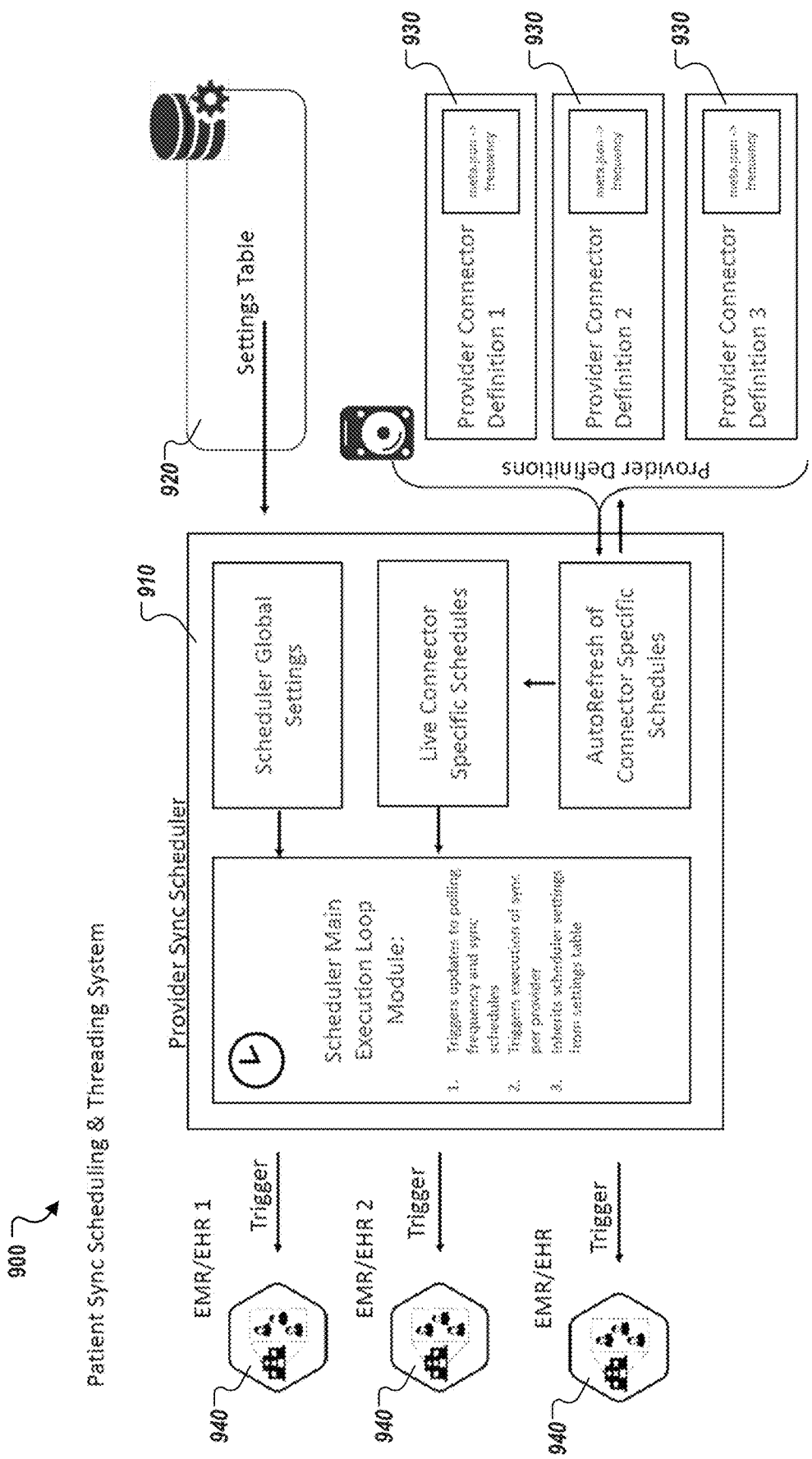
FIG. 9 depicts a non-limiting exemplary synchronization scheduling and threading system that may be implemented by the described data abstraction system to schedule the execution of data provider connector modules.

FIG. 9 depicts an example synchronization scheduling and threading system 900 that may be implemented by the described data abstraction system to schedule the execution of data provider connector modules, such as the data provider connector modules 142 of FIG. 1. As depicted, the synchronization scheduling and threading system 900 includes a provider synchronization scheduler 910, a setting table 920, provider connector definitions 930, and data providers 940. In some embodiments, the setting table 920 includes configurations and settings that the provider synchronization scheduler 910 inherits when executing. In some embodiments, the provider synchronization scheduler 910 is a time-based job scheduler, such as a CRON scheduler, that periodically updates and executes each of the connector modules. For example, provider synchronization scheduler 910 dynamically loads and refreshes the data provider connector modules based on the respective provider connector definitions 930. In such examples, each of the provider connector modules, once loaded, is the executed periodically based on the settings specified within its respective provider connector definitions 930. In some embodiments, the provider synchronization scheduler 910 includes a main execution loop module 912 that triggers updates to polling frequency and synchronization schedules for the data provider connector modules, triggers execution of the synchronization per data provider, and inherits scheduler settings from the settings table 930.

Figure 10:
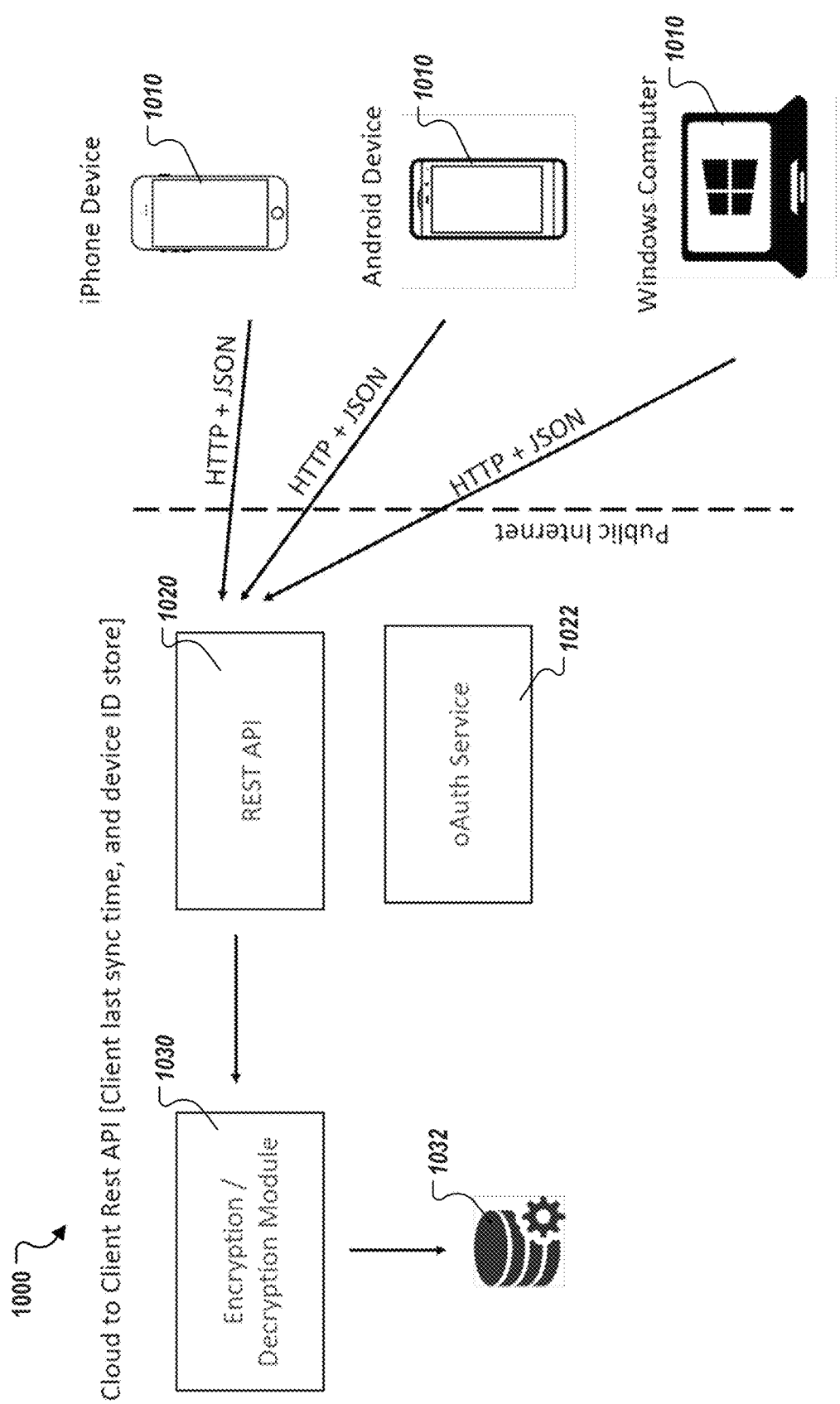
FIG. 10 depicts a non-limiting exemplary cloud to client REST API.

FIG. 10 depicts an example 1000 of a cloud to client REST API. The depicted example includes client devices 1010, a REST API 1020, an authentication service 1022, an encryption and decryption module 1030, and data store 1032. In some embodiments, client devices 1010 include mobile devices, such as iPhone® devices and Android® devices, and well as laptop and personal computer devices running Windows®. In some embodiments, the client devices 1010 execute a software client, such as software clients 110 of FIG. 1, that connect to the REST API 1020. In some embodiments, the software clients include standalone application executing on the client devices 1010. In some embodiments, the software clients include web browsers displaying a cloud-based portal, such as a patient portal.

In some embodiments, the REST API 1020, the authentication service 1022, and encryption and decryption module 1030 are components of a REST API, such as the REST API 120 of FIG. 1. In some embodiments, database 1032 is substantially similar to the administrative database 124 of FIG. 1. In some embodiments, the software clients executing on the client devices 1010 authenticate through the authentication service 1022 to establish a session with the REST API 1020. For example, a software client may provide a user's credentials and authenticate based on a defined authentication protocol. In some embodiments, the REST API 1020 retrieves the data record from the database 1032 that are accessible based on the provided credentials and provides the data records, but striped of the PHI, to the respective software client. In some embodiments, the database 1032 stores the data records in an encrypted state. In such embodiments, the encryption and decryption module 1030 is employed to encrypt and decrypt the stored data records.

Figure 11:
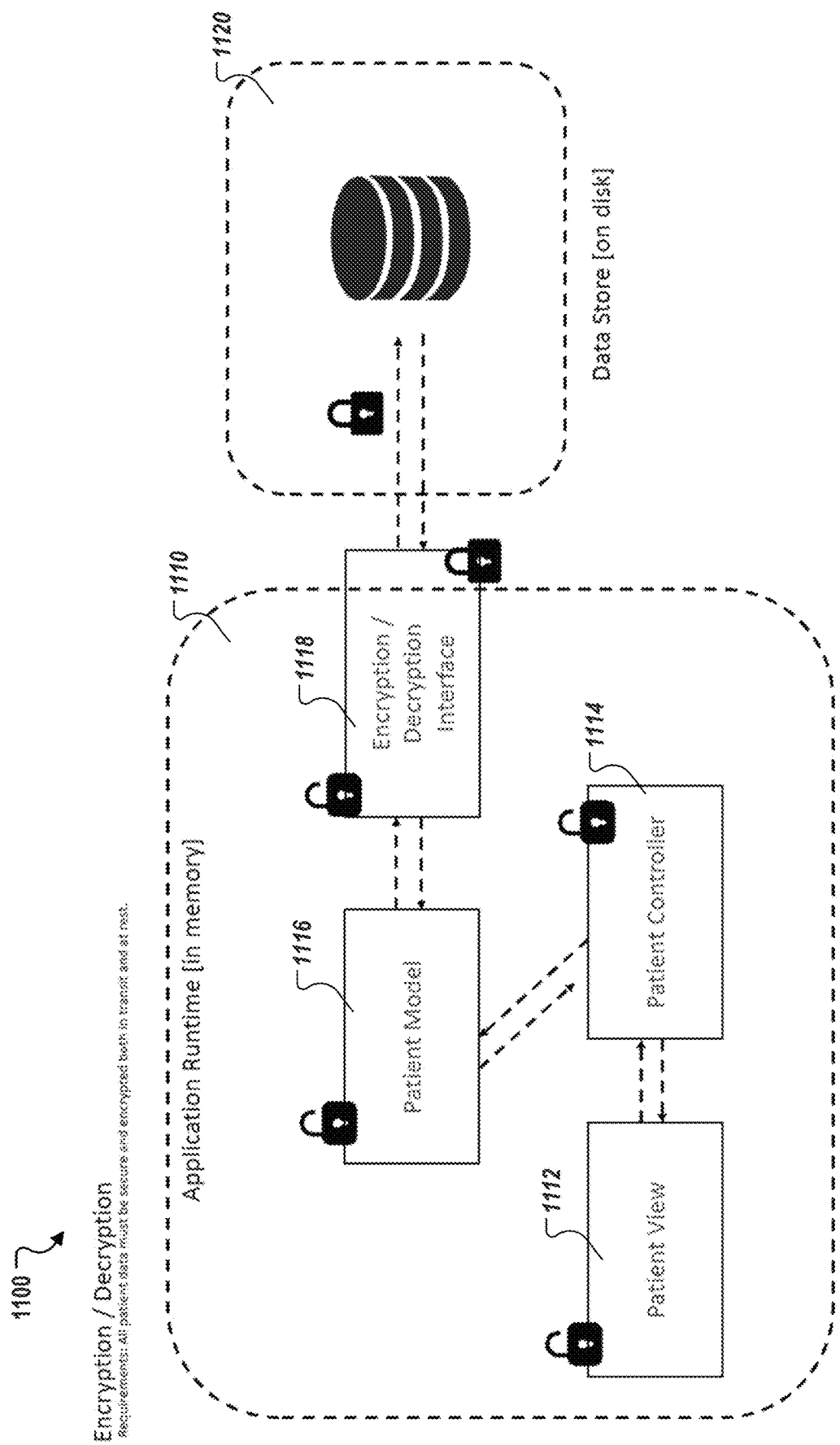
FIG. 11 depicts a non-limiting example of how and when data is encrypted within an application runtime and on a respective data store.

FIG. 11 depicts an example 1100 of how and when data is encrypted within an application runtime and on a respective data store. The depicted example 1100 demonstrates how a requirement that data records, such as patient data records, be encrypted and secure while in both transit and at rest (e.g., persisted in a data store) may be implemented. The depicted example includes an application runtime 1110 and a data store 1120. The data store 1120 may include any of the database and data stores discussed previously, such as the administrative database 124 of FIG. 1, where records encrypted before being persisted.

As depicted, the application runtime 1110 includes a patient view 1112, a patient controller 1114, a patient model 1116, and an encryption/decryption interface 1118; however, the application runtime 1110 may include any components of the described data abstraction system, such as the REST API 120 of FIG. 1, that load and pass data records between various system module loaded into memory. As depicted, the data records are passed unencrypted between the various modules loaded within the application runtime 1110. The encryption/decryption interface 1118 encrypts the data for storage to the data store 1120 and decrypts the data records when retrieved from the data store 1120.

Connector Loading from Disk Versus Database Performance Benchmarks

FIGS. 12A-12D depict various graphs that include measurements of example benchmarking data comparing the performance of implementations of the described data abstraction system where definitions of data provider connector modules were loaded from disk versus another means, such as from a database. The depicted data shows the memory usage, CPU usage, and execution times for the varied implementations.

The data depicted in FIGS. 12A-12D was collected from benchmarking counting solution implementations where a custom set of connector executors, one for the database and one for the disk, was employed. The benchmark testing was performed in a real-world testing scenario to ensure the system was tested both at scale and under appropriate stress. In the implementations, metrics collection counters were employed to measure various data points, such as start time, finish time, total execution time, CPU at execution time, and memory usage at execution time.

Figure 12A:
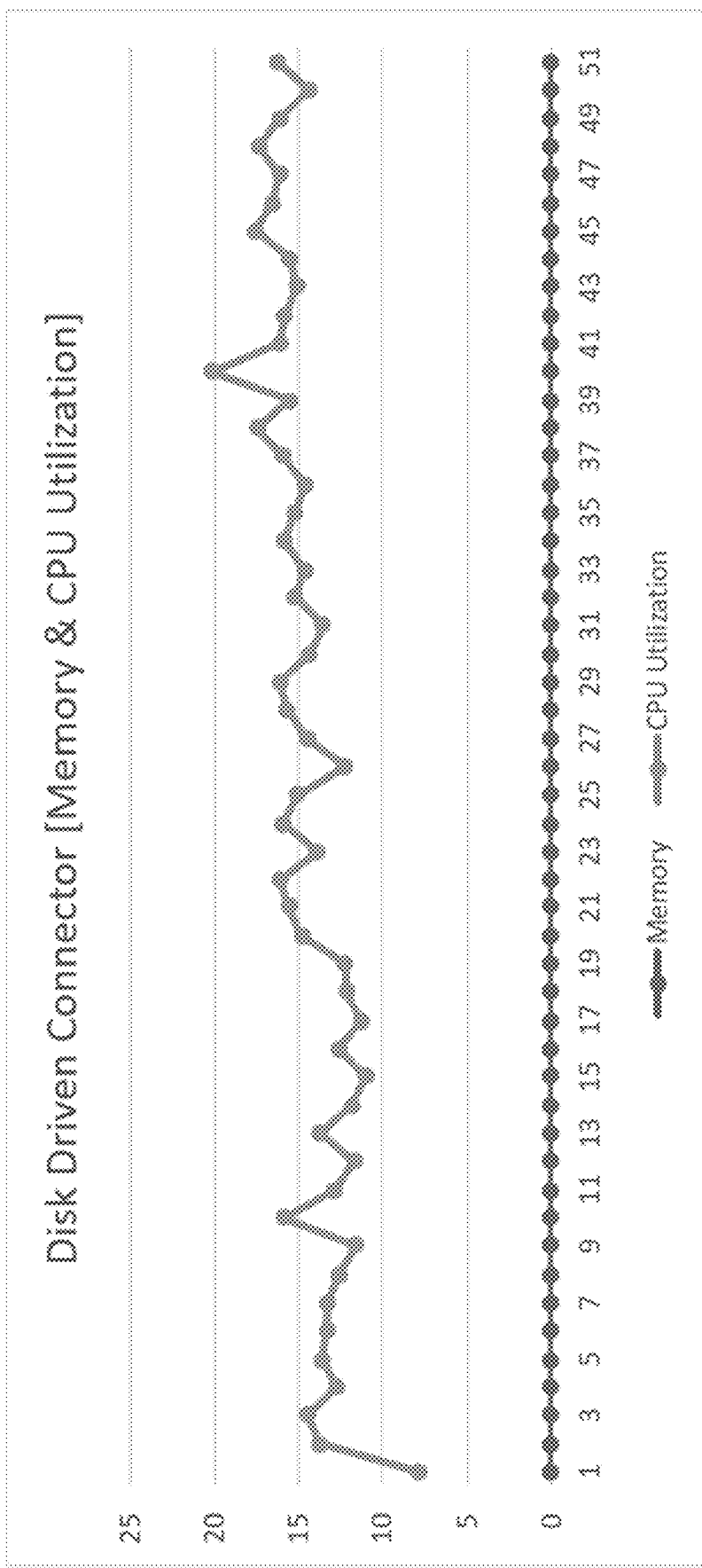
FIGS. 12A-12D depict various graphs that include measurements of example benchmarking data.
Figure 12B:
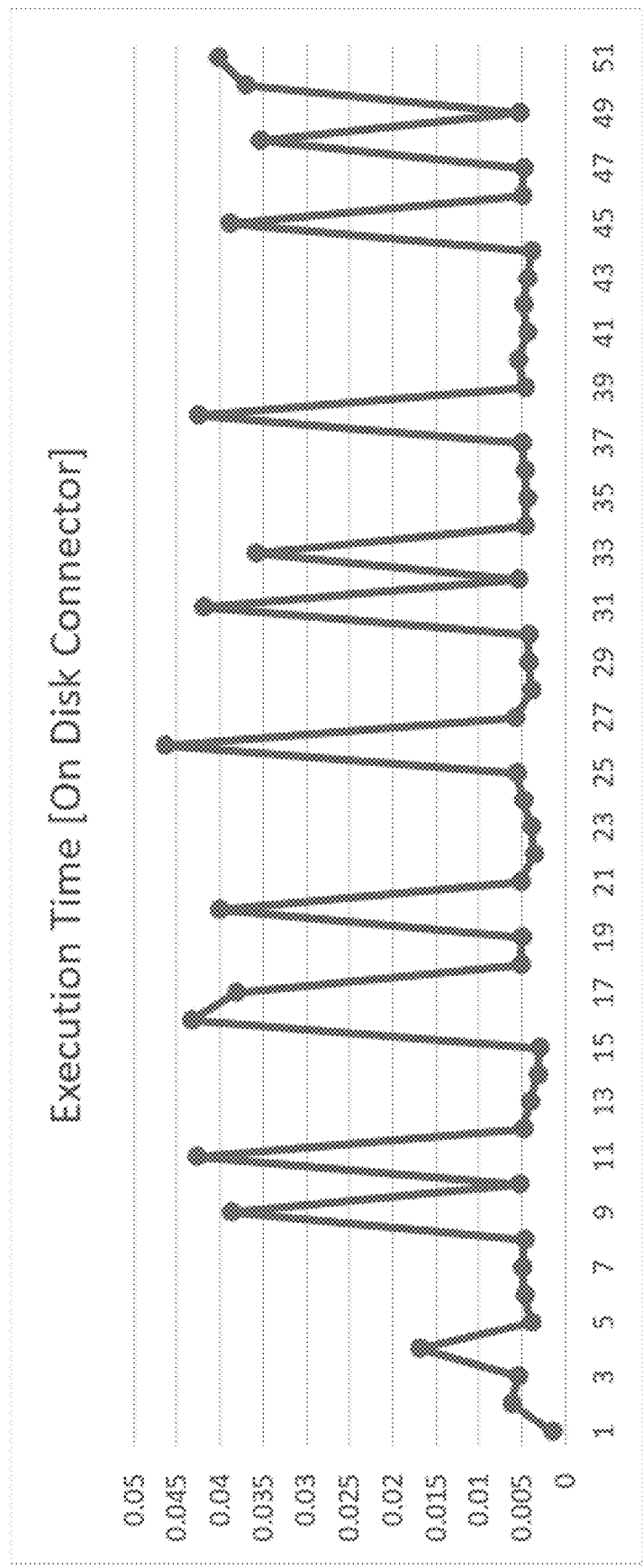
Figure 12C:
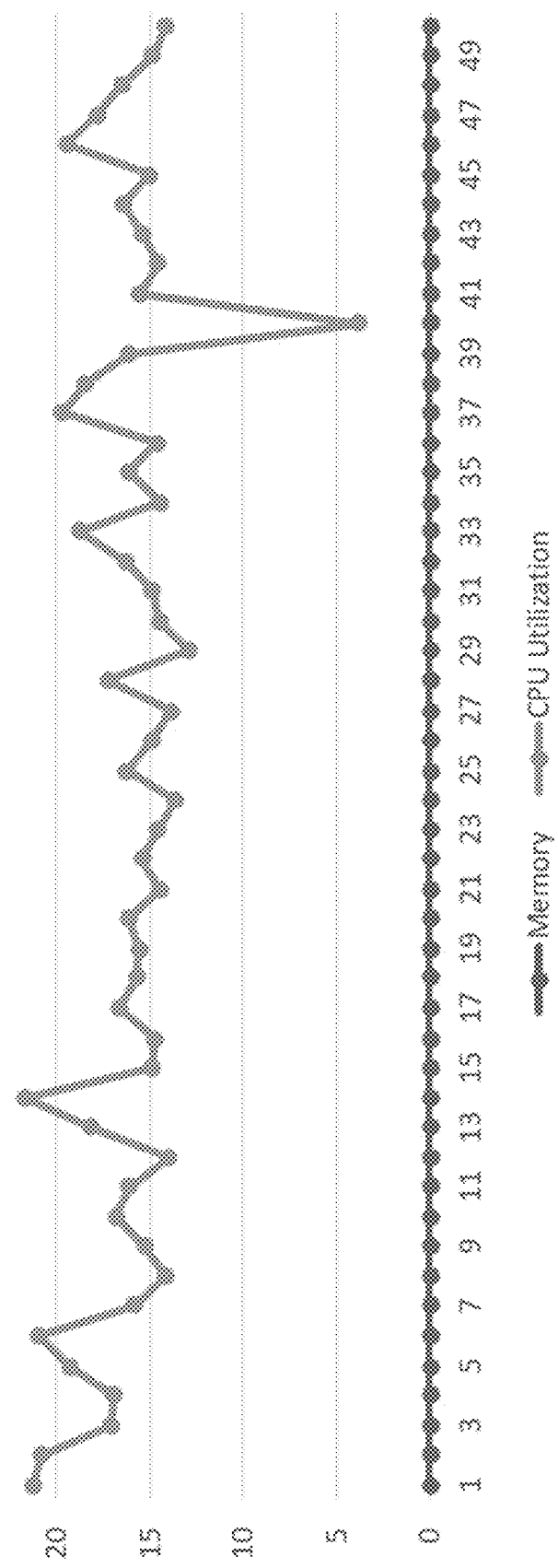
Figure 12D:
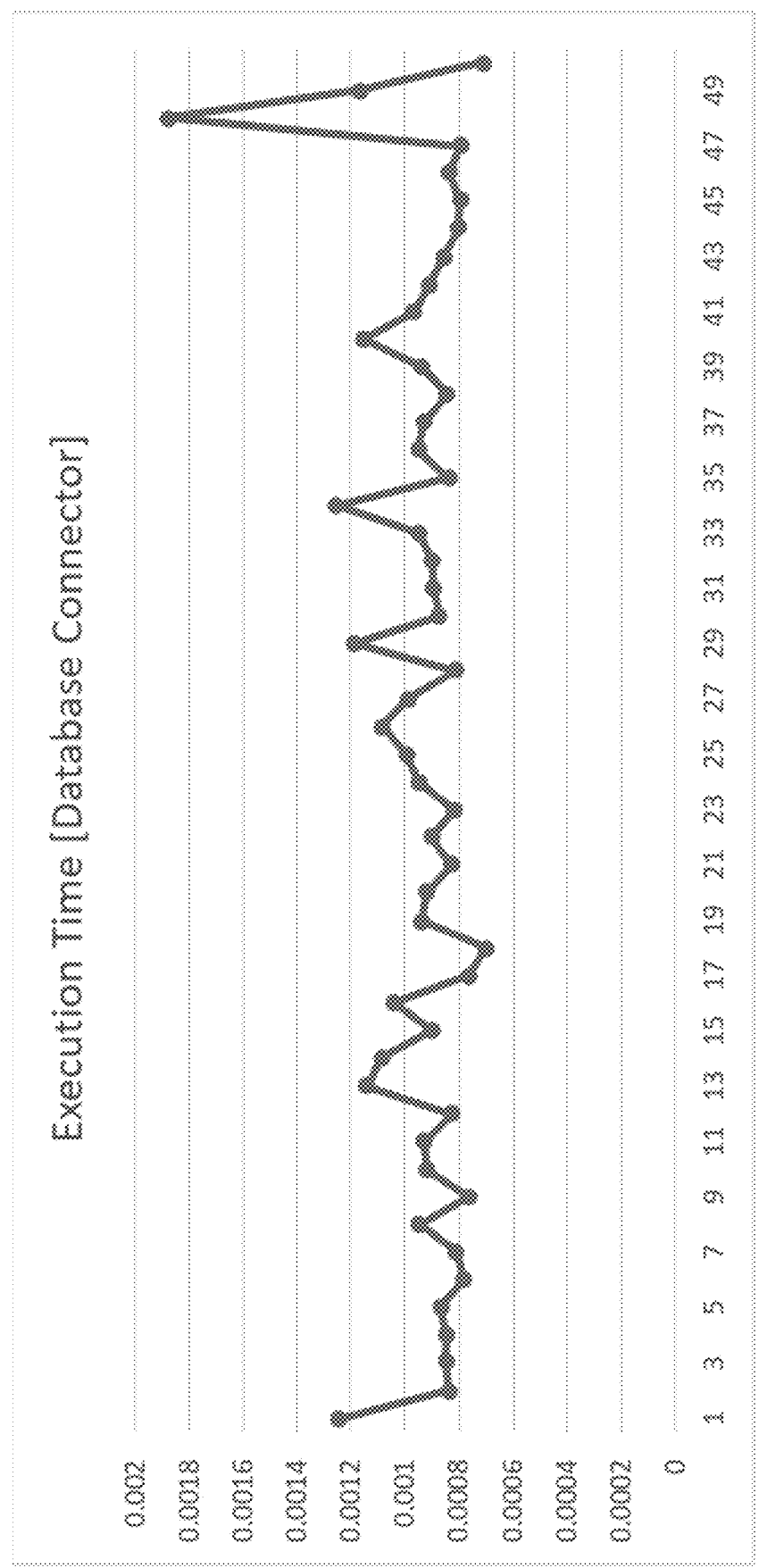

Graphs 1200 and 1210, depicted in FIG. 12A and FIG. 12B respectively, represent data points collected from an implementation of the described data abstraction system where definitions of data provider connector modules were loaded from disk (disk implementation). Graphs 1220 and 1230, depicted in FIG. 12C and FIG. 12D respectively, represent data points collected from an implementation of the described data abstraction system where definitions of data provider connector modules were loaded from a database (database implementation).

The benchmarking data demonstrates a number of tradeoffs that show that the disk implementation, as compared to the database implementation, is performant and provides a solid mechanism for communicating to external data sources. Moreover, as shown by the benchmarking data, the disk implementation provides technical improvements over a system that employs the database implementation for storage and retrieval of definitions for data provider connector modules. For example, the disk implementation 1) provides the ability for offline code access, 2) provides a modular way for managing the execution of connector commands and syncs with no specific additional layers of security required due to modular design, 3) performs well under load because scaling is done horizontally, and 4) ensures fault tolerance (e.g., when one node fails that doesn't mean the others will also fail). These technical improvements are not provided (or are provided to a less performative manner) for a system that employs the database implication for storage and retrieval of definitions for data provider connector modules. Further, the database implementation 1) requires additional security layers (when compared to the disk implementation) to ensure the connector code is not compromised, and 2) is not as scalable as the disk implementation due to the lack of encapsulation and modular design.

Benchmarking of In-Memory Database Implementation for Provider Connector Modules FIGS. 13A-13G depict various graphs that include measurements of example benchmarking data comparing the performance of implementations of the described data abstraction system where provider connector modules load and update patient data employing an in-memory database versus a database implementation reading/writing to disk. The benchmark testing was performed in a real-world testing scenario to ensure the system was tested both at scale and under appropriate stress. Ensuring that the database layer can handle the requested load was a key metric gathered. When performing the database benchmark analysis, a trend in speed of transaction write time to type of medium being written to was observed. The analysis shows a drastic performance (e.g., speed) improvement for the in-memory implementations as compared to a disk implementation.

Figure 13A:
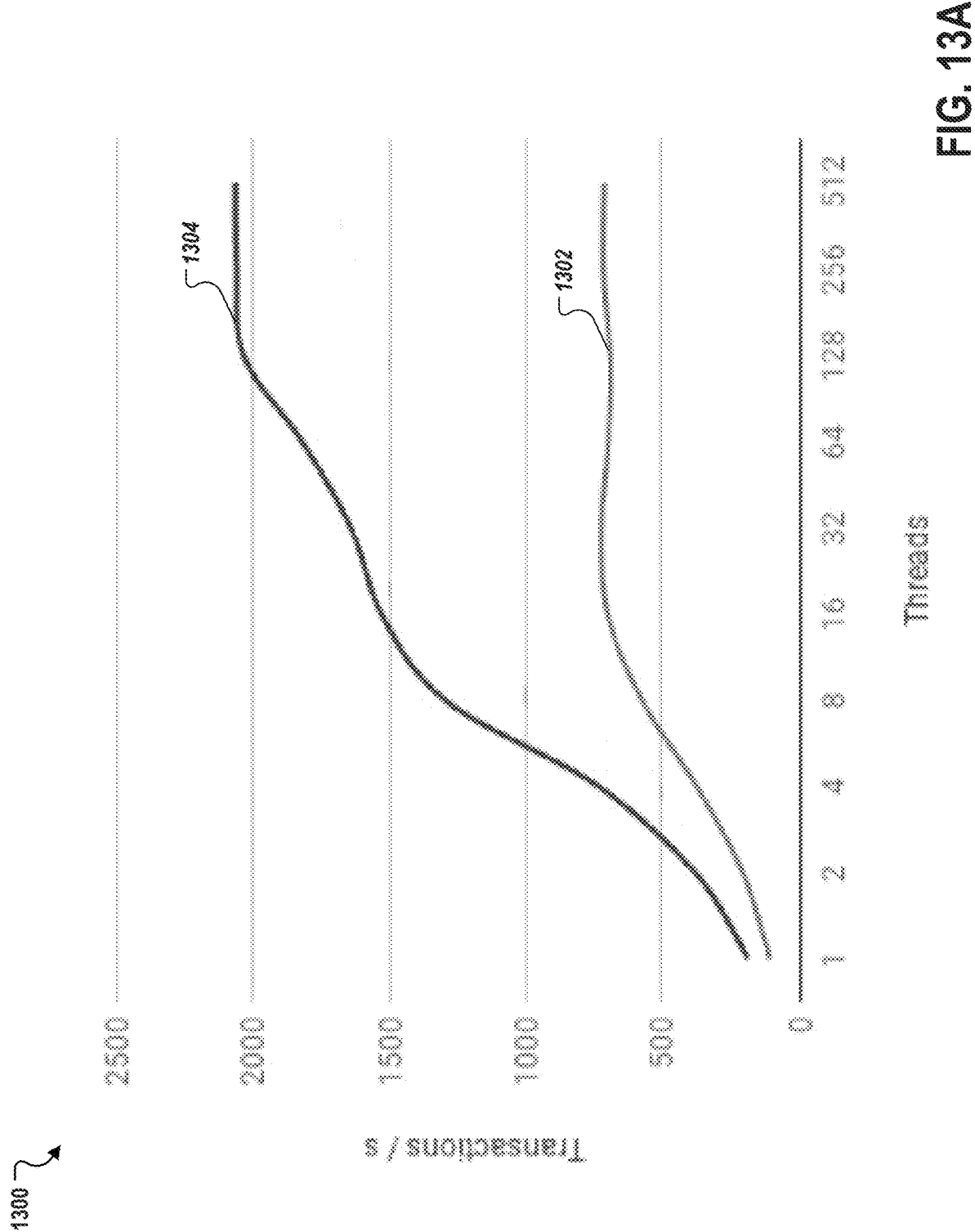

Graph 1300, depicted in FIG. 13A, includes the number of transaction writes per second along the vertical axis with the number of simultaneously executing threads depicted along the horizontal axis. The graph 1300 includes the in-memory implementation 1304 and the disk implementation 1302. The depicted data shows the scaling and save time performance deficits leveling off as the scaling increases, and also as transactions/threads increase. For example, as depicted in graph 1300 the number of transaction writes per second maxes with 16 threads at approximately 700 whereas the number of transaction writes per second continues rise to over 2000 and does not cap until 256 threads are spun.

Figure 13B:
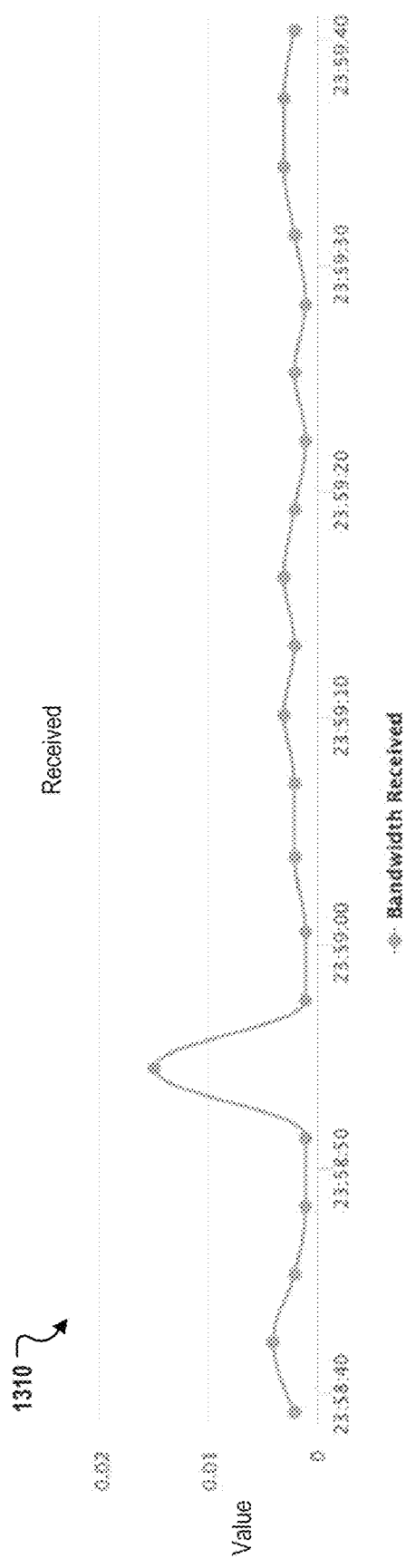
Figure 13C:
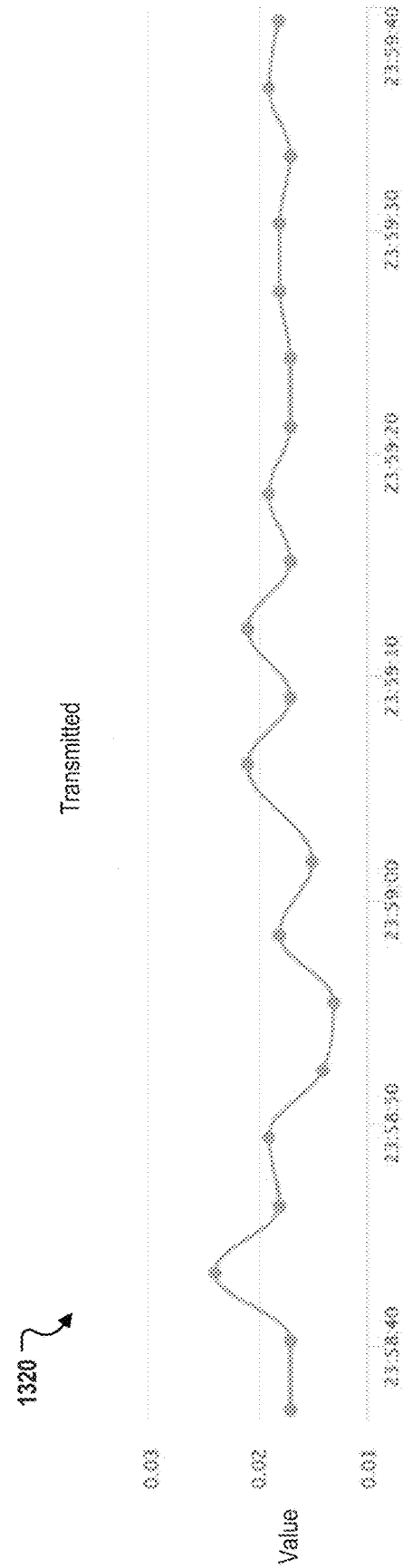

Graphs 1310 and 1320, depicted in FIGS. 13B and 13C respectively, include the results of the bandwidth monitoring during the execution of the performance benchmarks. The data was collected to show that no unexpected spikes in bandwidth occurred during the execution of the tests. Graph 1310 includes the collected data regarding the bandwidth received during the testing while graph 1320 includes the collected data regarding bandwidth transmitted. The information included in graphs 1310 and 1320 are representative of a generally consistent bandwidth usage during the testing time period with no unexpected variations in usage. The data shows that even under appropriate load, the described system's connections remain stable and performant.

Figure 13D:
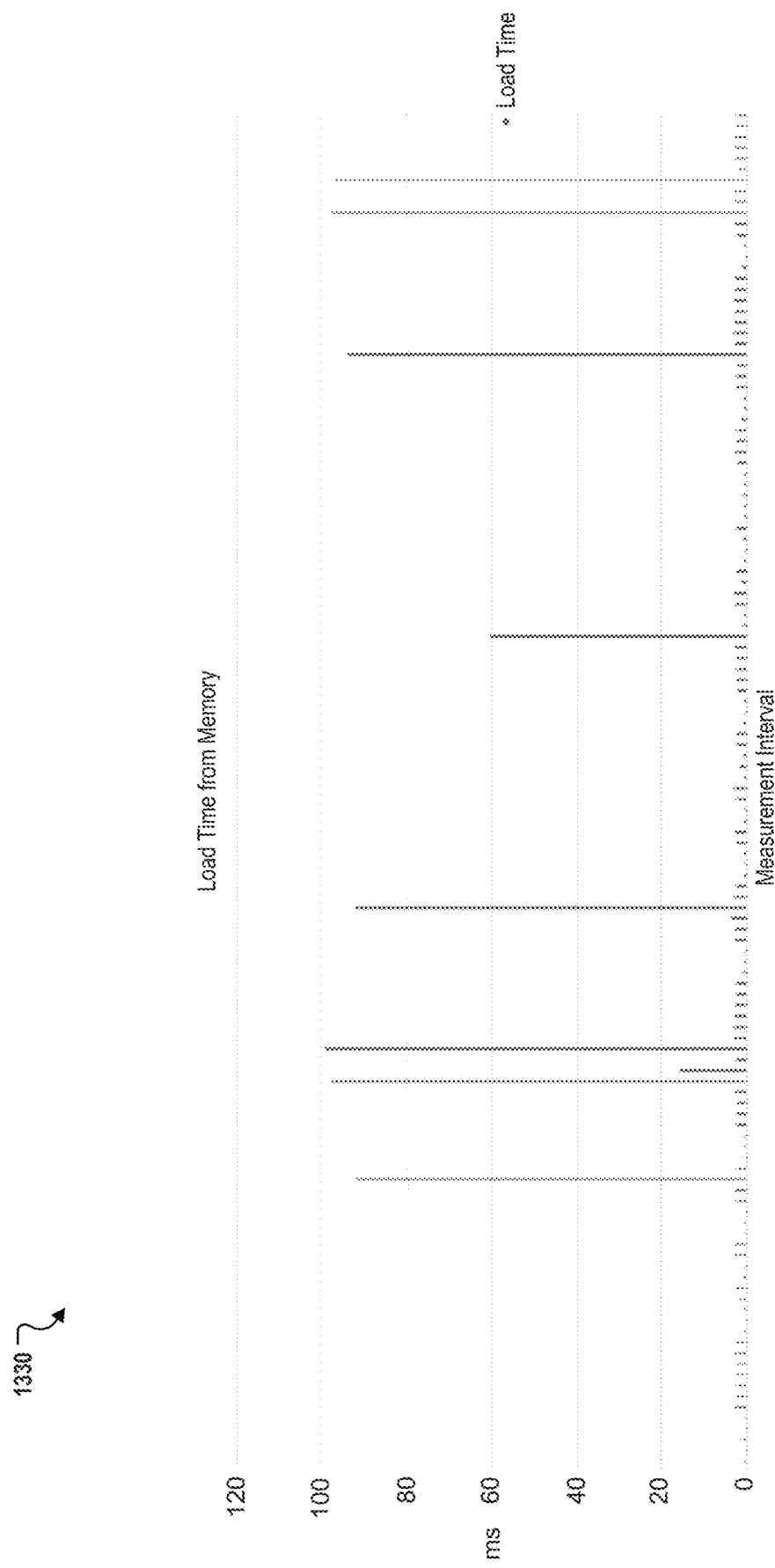
Figure 13E:
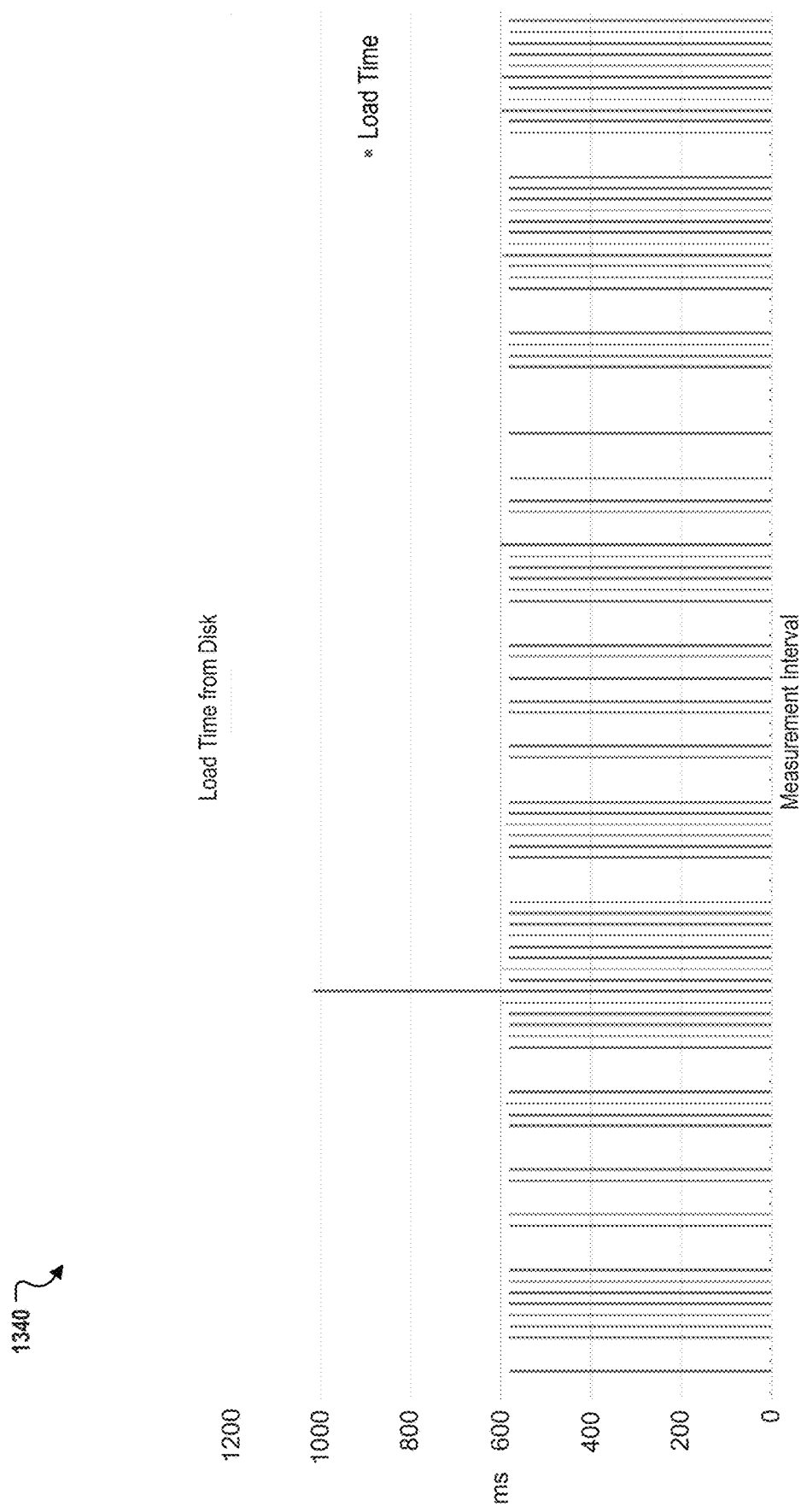

FIGS. 13D and 13E each depicted various graphs that include load time data of patient data into memory through the provider connector collected during the performance benchmarking. Graph 1320, depicted in FIG. 13D, includes the load time performance data for the in-memory database implementation. When running the performance testing scenarios against the cloud nodes, the data shows that the performance of in memory loading of patient data was significantly more performant than that of the disk implementation. The data shows that this performance disparity was due to the throughput requirements of physical writes to a hard drive in the disk implementation which are not significantly present in the in-memory implementation. The timings were also significant in difference. As shown in Graph 1320, barring the occasional abnormality spiking to about 100 milliseconds (ms), the general average of memory load times was noticeably cut by a factor of 40 as compared to the data included in graph 1330. These occasional spikes in resource usage represent either flukes in the timing calculations, or potentially an additional page load occurring in parallel from an outside source. Generally, the times calculated remained steady throughout the process as the data included in graph 1320 shows that the average loading of patient data in milliseconds was under 10 ms.

Graph 1330, depicted in FIG. 13E, includes the load time performance data for the disk database implementation. As mentioned above, the loading of patient record data via disk was significantly slower due to the round-trip time for retrieving records from the appropriate disk sector and populating the appropriate memory slot with the relevant data. The data included in graph 1303 shows that this additional time made the average loading of patient data around 500 ms or about half a second per record. As such, the benchmarking data included in graphs 1320 and 1330 comparing load time performance of the described data abstraction system show that the in-memory database implementation is faster (under 10 ms compared to around 500 ms), and thus able to process a larger number of transactions for a given timeframe, than the database implementation reading/writing to disk.

Figure 13G:
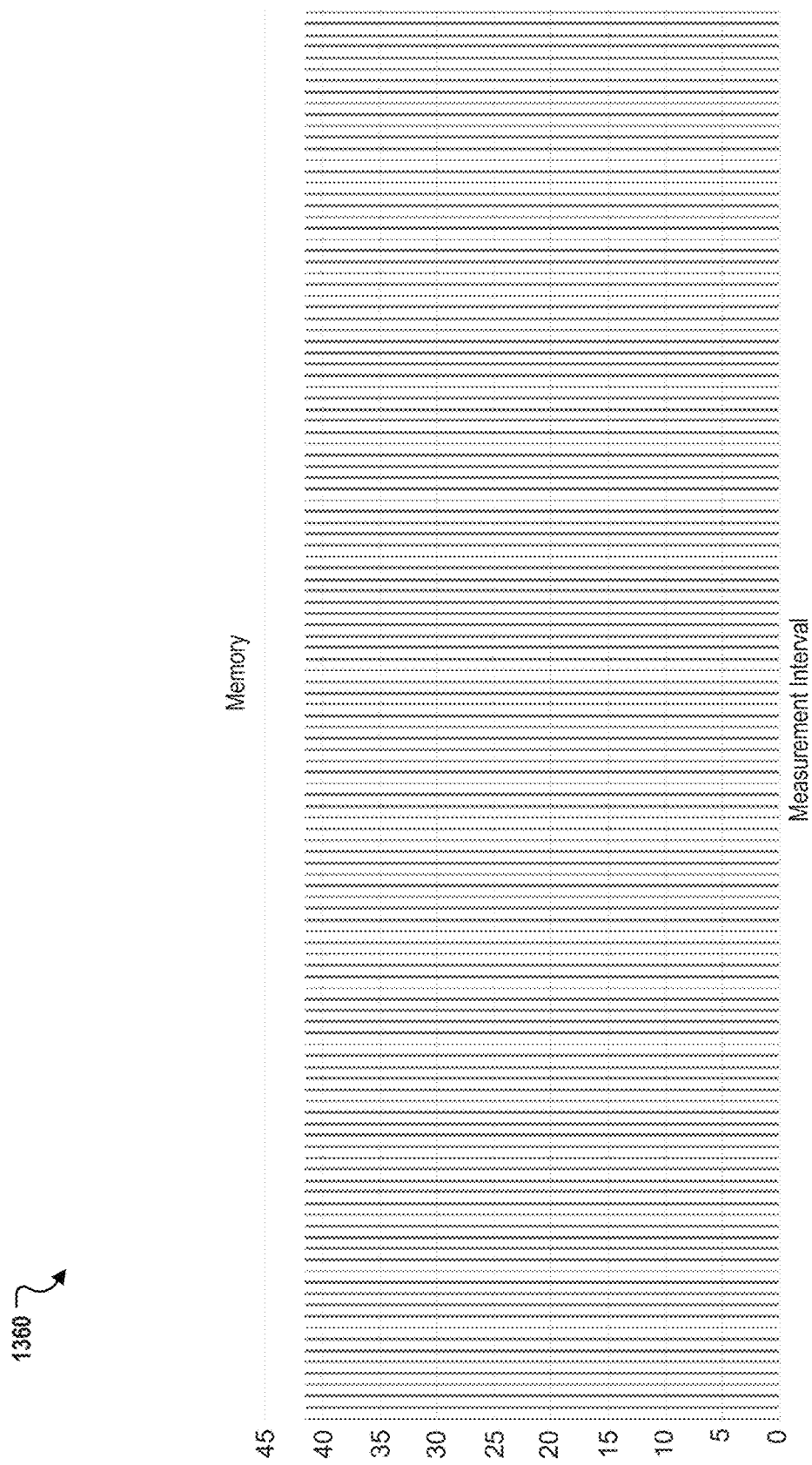

FIGS. 13F and 13G depict graphs 1350 and 1360 respectively. Graph 1350 includes CPU performance data collected during benchmarking while graph 1360 includes memory usage collected during benchmarking. This helped gauge the system's performance when importing patient data, updating patient data, and recording the benchmark results. While executing the performance benchmark tests, the CPU averaged a 40 percent, usage general consistency. This includes roughly 15 percent in system overhead. CPU and memory both spiked accordingly regardless of whether the data was loaded from disk or from memory, averaging 40 percent usage in RAM/MEMORY and 13 percent CPU usage respectively). The memory usage data included in graph 1360 show the memory spiking during patient retrieval, and then decreasing after completed. This consistent "zig-zag" is akin to loading and unloading data. The important measurement here is not the zig-zags but rather the consistent 40 percent usage during operation of patient data.

The information included in Graphs 1300-1360 shows that the implementation of the described system, which includes provider connector modules employing an in-memory database for the loading and updating of patient data versus a database implementation reading and writing to disk, 1) scales more effectively when infrastructure and hardware are added to the solution in response to an increase in patient activity; 2) scales effectively in both a single node and multi-node implementation; 3) manages an increased amount of throughput (e.g., processes faster) without issue; 4) scales equally as well as the software implementation and can handle stress and load; 5) scaling horizontally to meet the demands of large EMR providers; and 6) handles traffic more efficiently.

Administrative Portal

FIGS. 14A-14G depict various non-limiting example pages of an administrative portal, such as the administrative portal 122 of FIG. 1, provided to user devices by the described data abstraction system. In some embodiments, the administrative portal includes a web-based graphical user interface (GUI) that allows providers to synchronize data to software clients, such as software clients 110 of FIG. 1, pull client data from the connector software, and manually enter and record patient data. In some embodiments, the administrative portal employs a REST API, such as REST API 120 of FIG. 1. In some embodiments, the administrative portal provides granular controls over encryption functionality. In some embodiments, the administrative portal is provided to ensure HIPAA security compliance. For example, the controls provide providers the ability to define (at a field level) which specific data should be encoded.

In some embodiments, the administrative portal provides the providers with the ability to administer the accounts of the clients. Such functionality may include, 1) creating accounts, 2) record pulls from providers (e.g., in read-only mode), 3) synchronize data to target account's devices, 4) manage and update personal information (e.g., name, address, phone number, and so forth), and provide password or pin unlock services to patients. In some embodiments, administrative portal provides access to manage accounts, and perform basic administrational duties for those accounts, as well as a bridge between the client applications and provider data feeds. Through a UI, an administrator or provider interface will have, by way of non-limiting examples, the following capabilities: 1) login and logout; 2) create client accounts; 3) remove client accounts; 4) edit client location and personal information; 5) request a sync of medical records for a client account; 6) perform clean-up operations (e.g., clearing of cache); 7) view client last login, last sync and related authentication stats; 8) enforce password alteration requirements (e.g., user must change pin on next login); 9) perform password and authentication maintenance for client accounts (e.g., set new password); 10) add and remove other administrator accounts; and 11) manage provider/connector availability (e.g., enable, disable, remove, test, add, and so forth).

In some embodiments, the administrative portal provides a bridge to data provider connector modules executed by the described system. For example, in some embodiments, the administrative portal provides access to various metrics for each of the bridge connectors as well as the system as a whole. Such metrics can include, by way of non-limiting examples: 1) number of total client accounts; 2) most recent sync information for each provider connector; 3) basic sync performance statistics for each provider connector; 4) a log of administrator access attempts (e.g., failed and successful) and 5) any other relevant statistics that would be useful to an administrator.

Figure 14A:
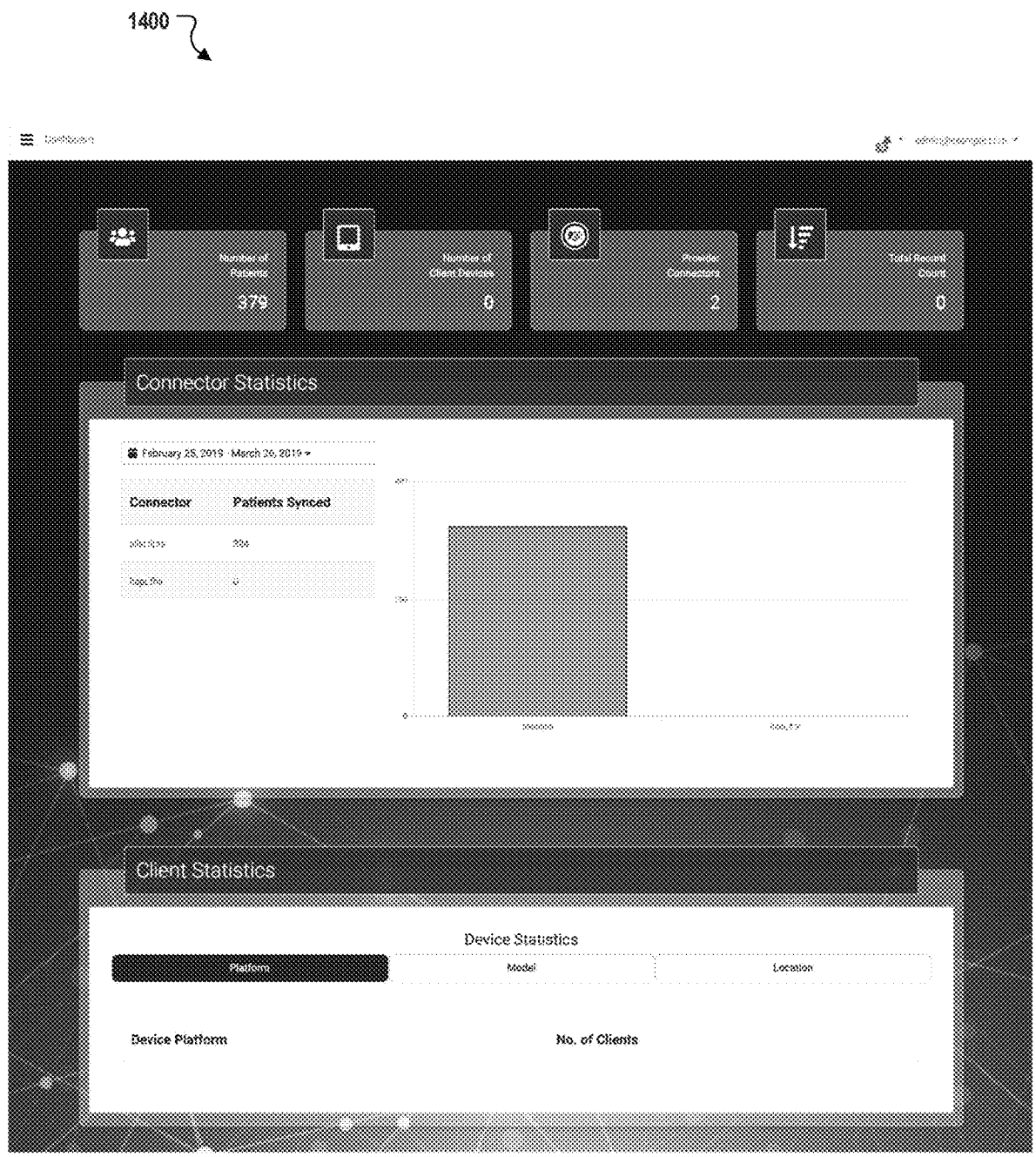

FIG. 14A depicts an example Admin/Cloud Dashboard page 1400 that can provide, for example, system usage statistics.

Figure 14B:
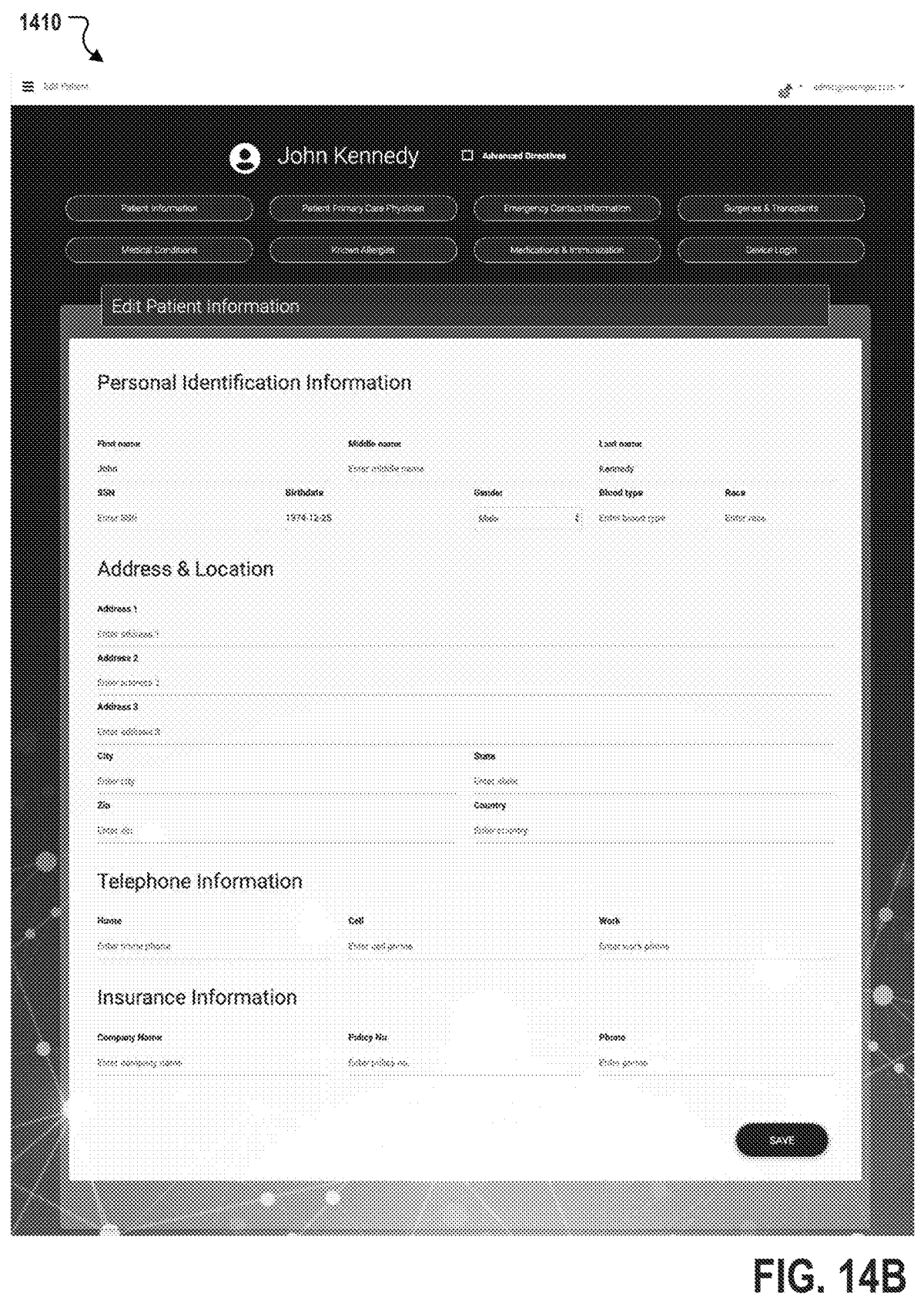

FIG. 14B depicts an example Admin/Cloud Patient Drill Down page 1410 that can provide, for example, detailed patient specific data and enables editing of same.

Figure 14C:
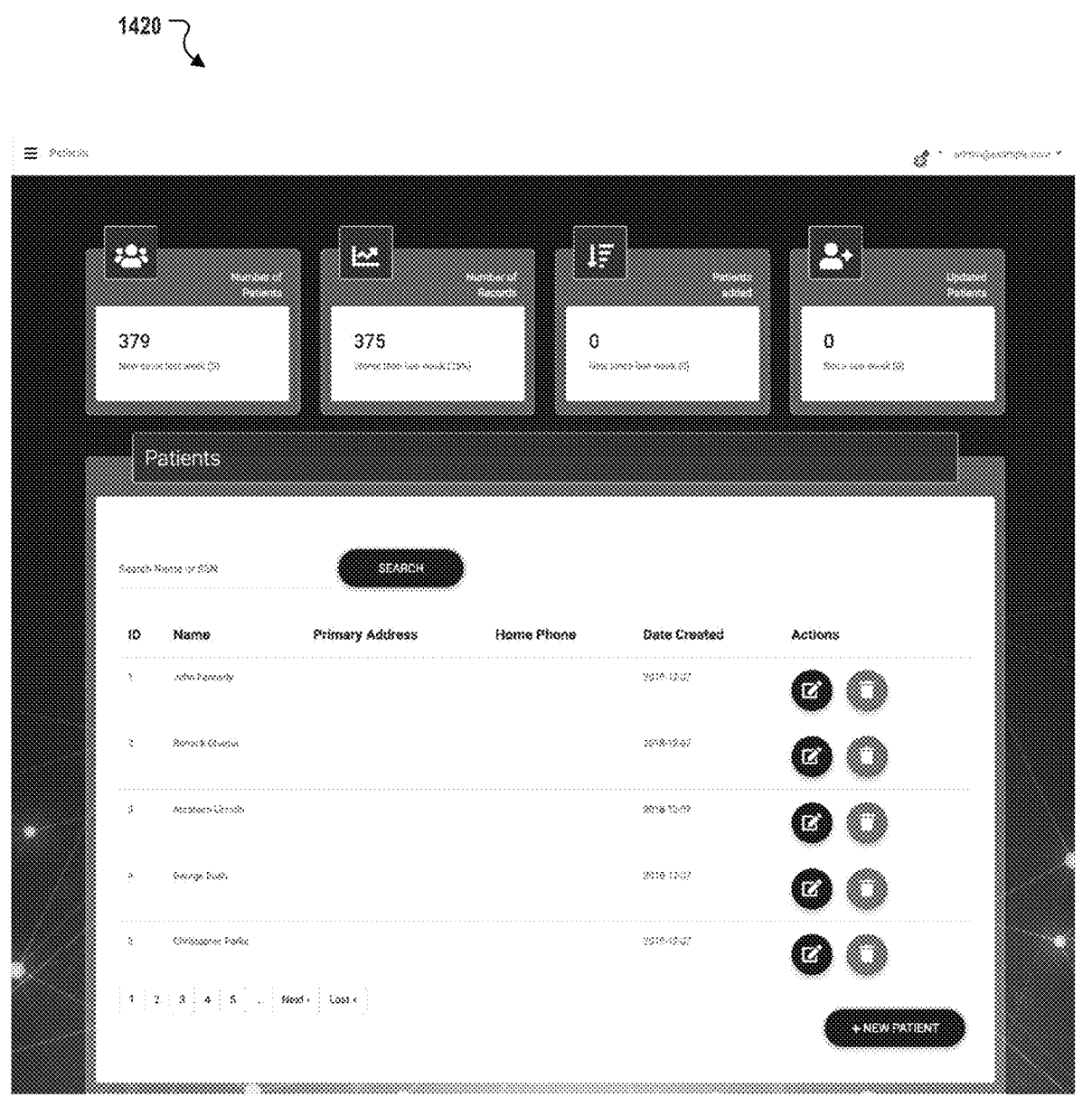

FIG. 14C depicts an example Admin/Cloud Patients page 1420 that can provide, for example, summary information for registered patients.

Figure 14D:
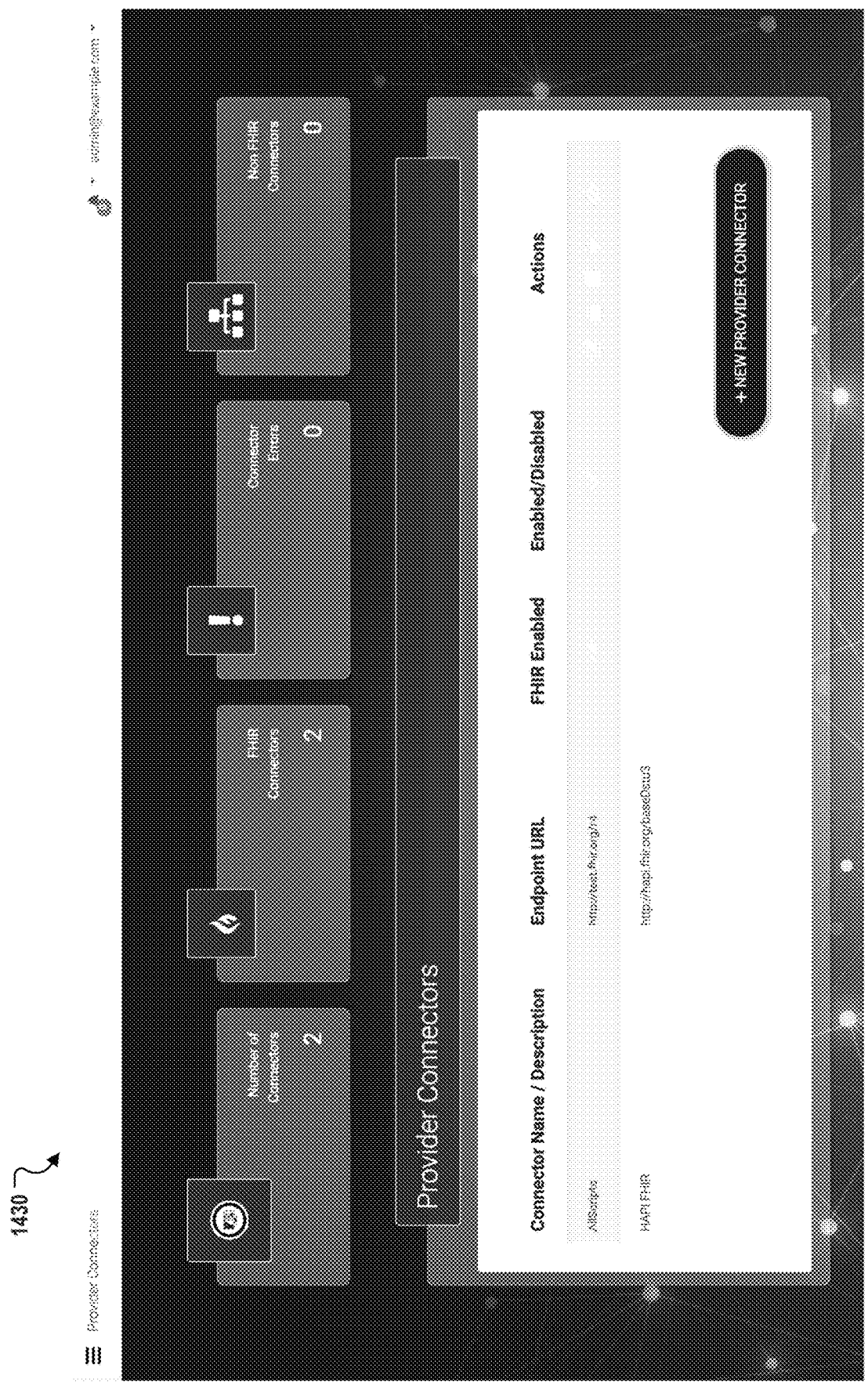

FIG. 14D depicts a non-limiting an example of an Admin/Cloud Provider Connectors page 1430 that can provide, for example, detailed connector information.

Figure 14E:
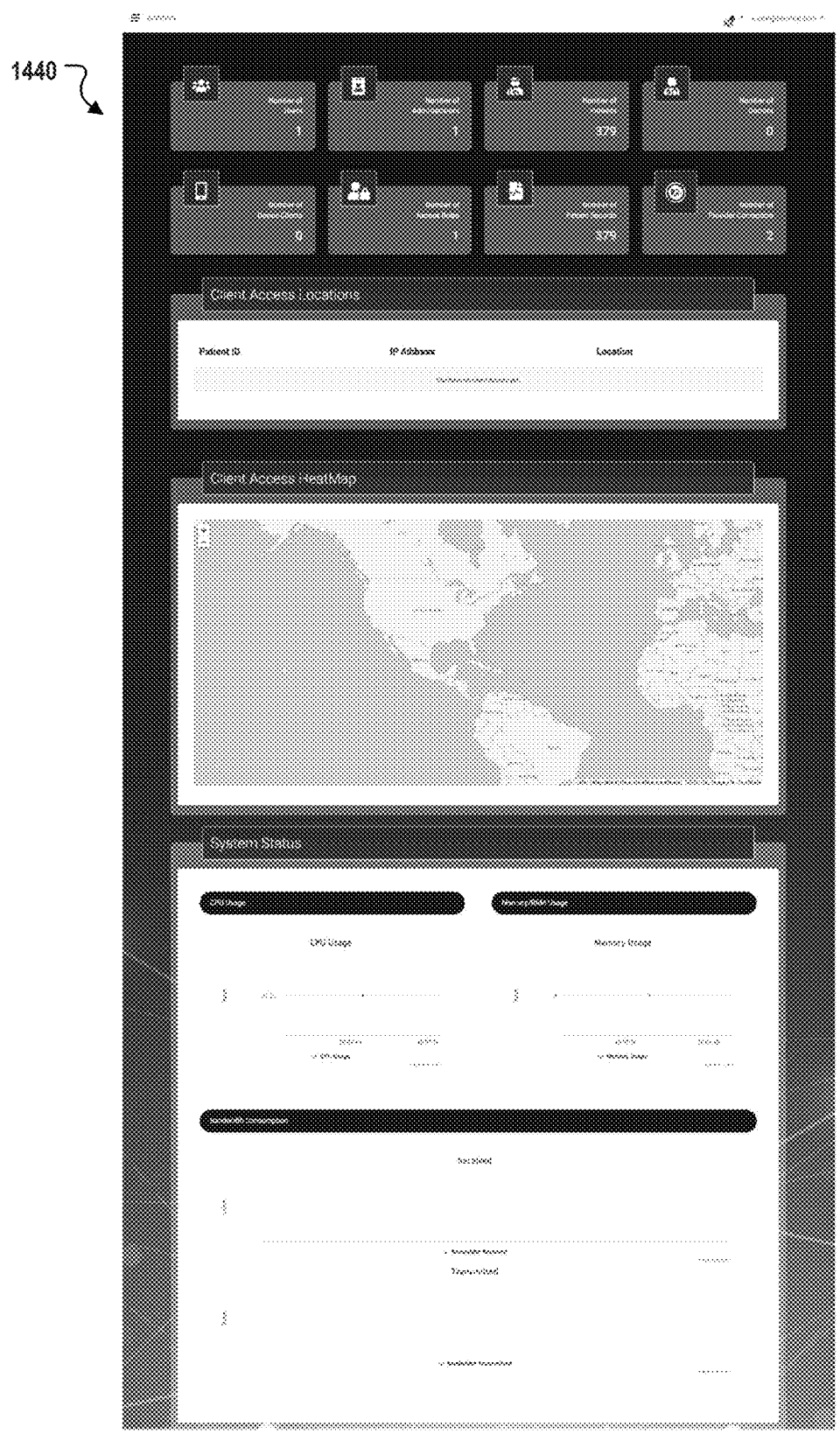

FIG. 14E depicts a non-limiting an example of an Admin/Cloud Statistics page 1440 that can provide, for example, client and system operational statistical detail.

Figure 14F:
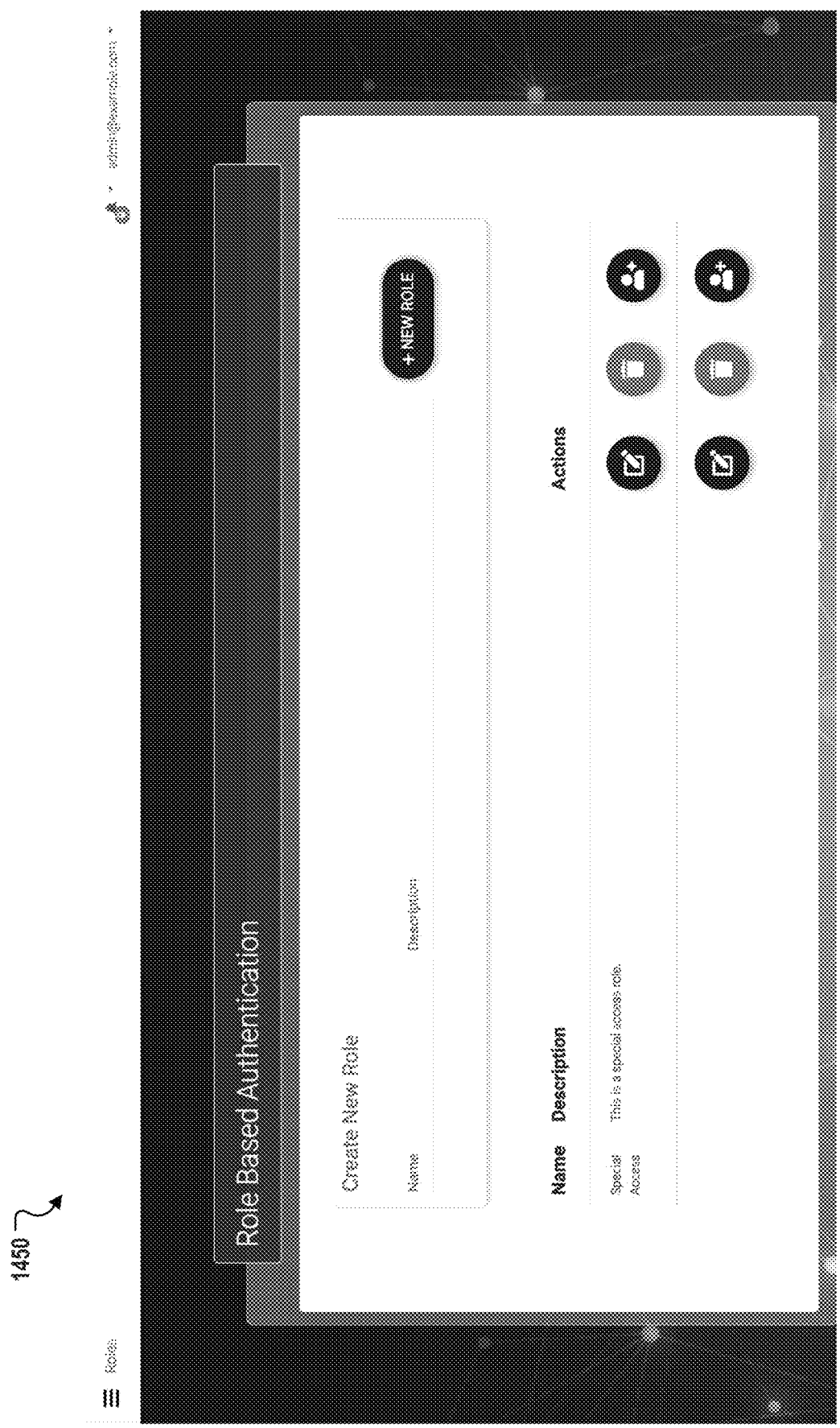

FIG. 14F depicts a non-limiting an example of an Admin/Cloud Roles page 1450 that can provide, for example, role creation functionality and access to definitions.

Figure 14G:
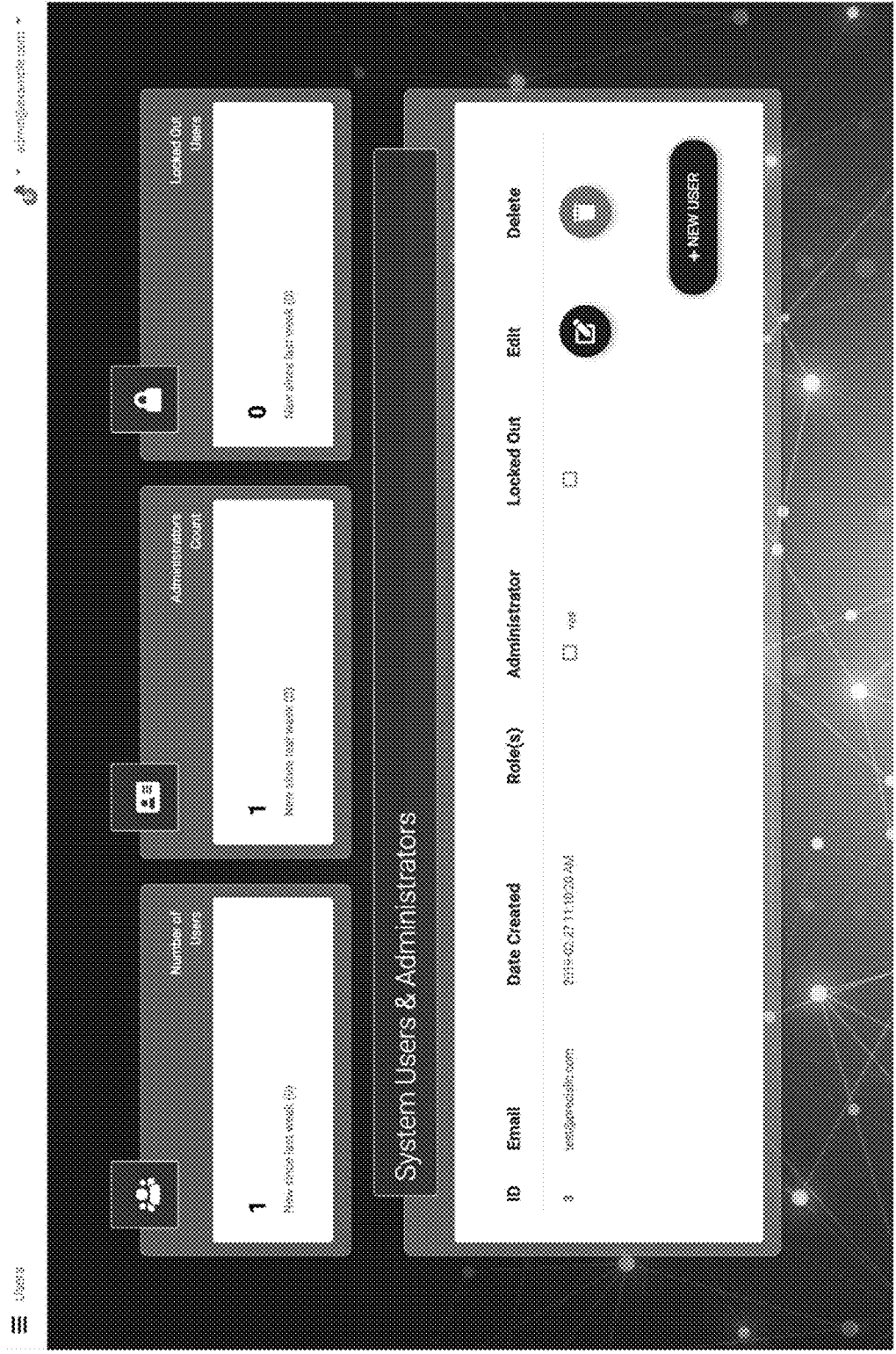

FIG. 14G depicts a non-limiting an example of an Admin/Cloud Users page 1460 that can provide, for example, user detail and status information.

Patient Portal

FIGS. 15A-15D depict various non-limiting example pages of a patient portal, such as the patient portal 124 of FIG. 1, provided to user devices by the described data abstraction system. In some embodiments, the patient portal includes a web access point that allows users (e.g., patients) to log in and view their patient data received by the described system. In some embodiments, a patient portal includes a secure website or mobile application that gives patients convenient access to personal health information from anywhere with an Internet connection. Using, for example, a secure username and password, patients can view health information such as: recent doctor visits, discharge summaries, medications, immunizations, allergies, lab results.

Figure 15A:
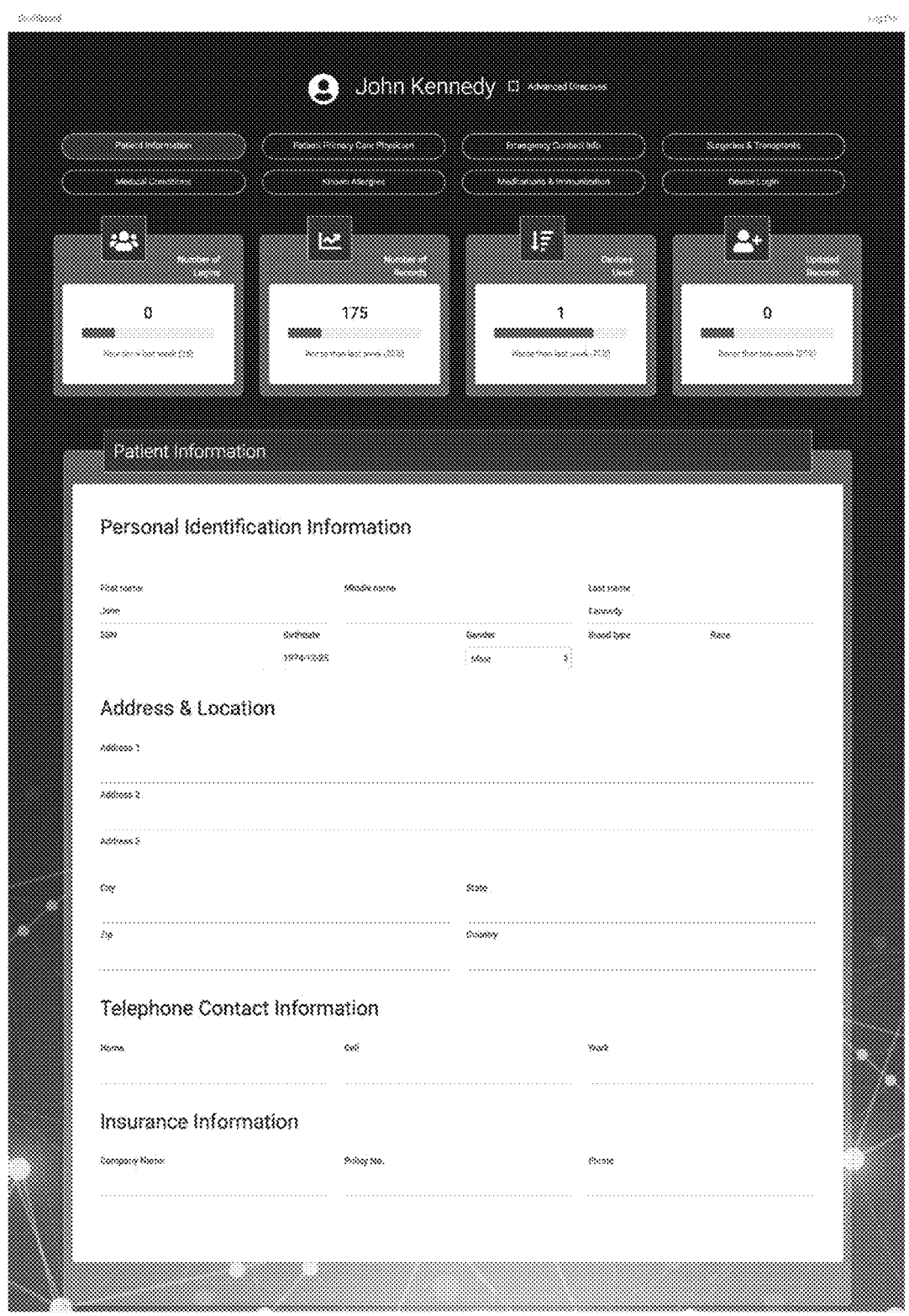
FIGS. 15A-15D depict various non-limiting exemplary pages of a patient portal provided to user devices by the described data abstraction system.

FIG. 15A depicts a non-limiting an example of a Patient Portal Patient Information page 1500 that can provide, for example, statistics and personal patient data.

Figure 15B:
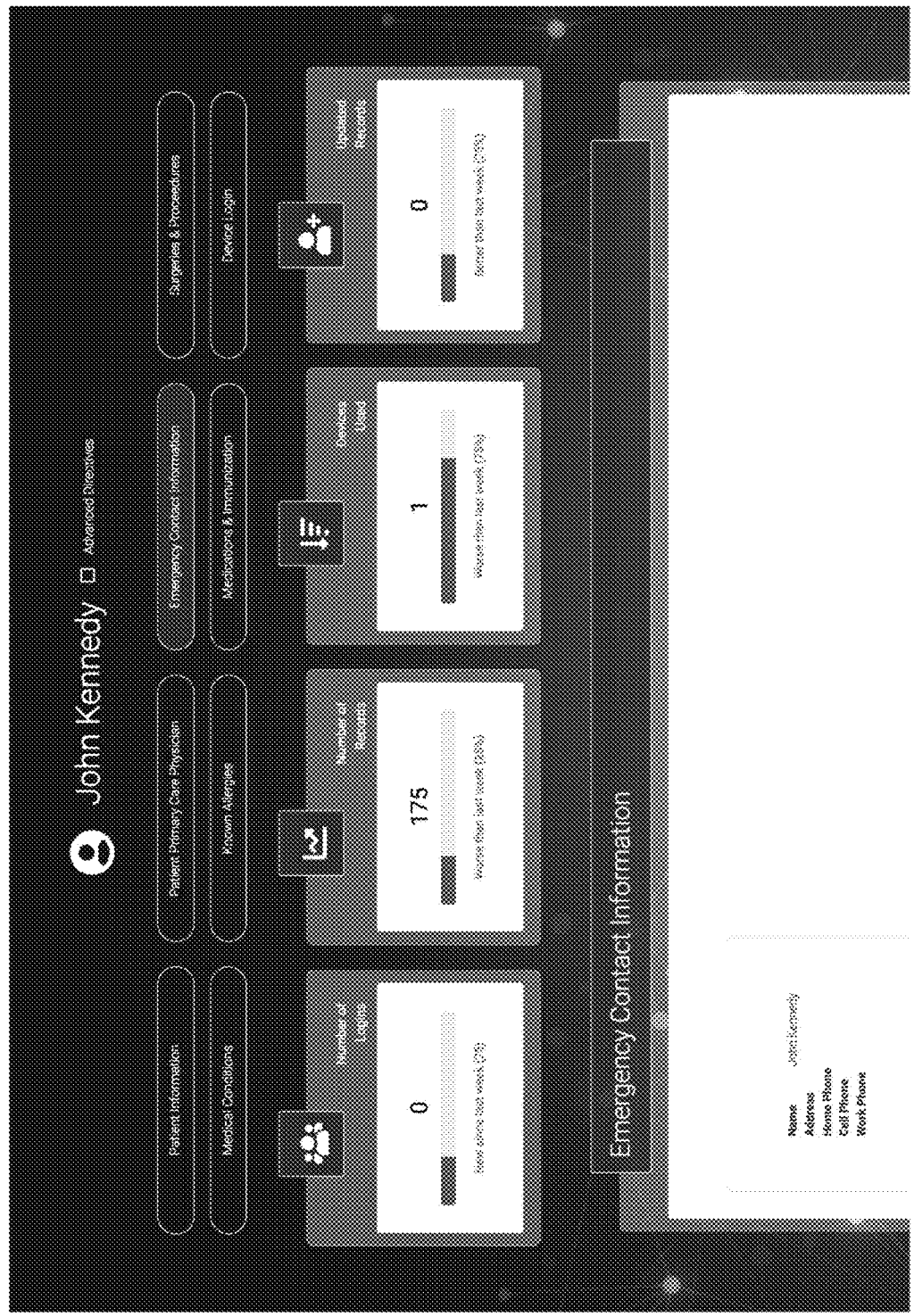

FIG. 15B depicts a non-limiting an example of a Patient Portal Emergency Contact Information page 1510 that can provide, for example, emergency contact information for a specific patient.

Figure 15C:
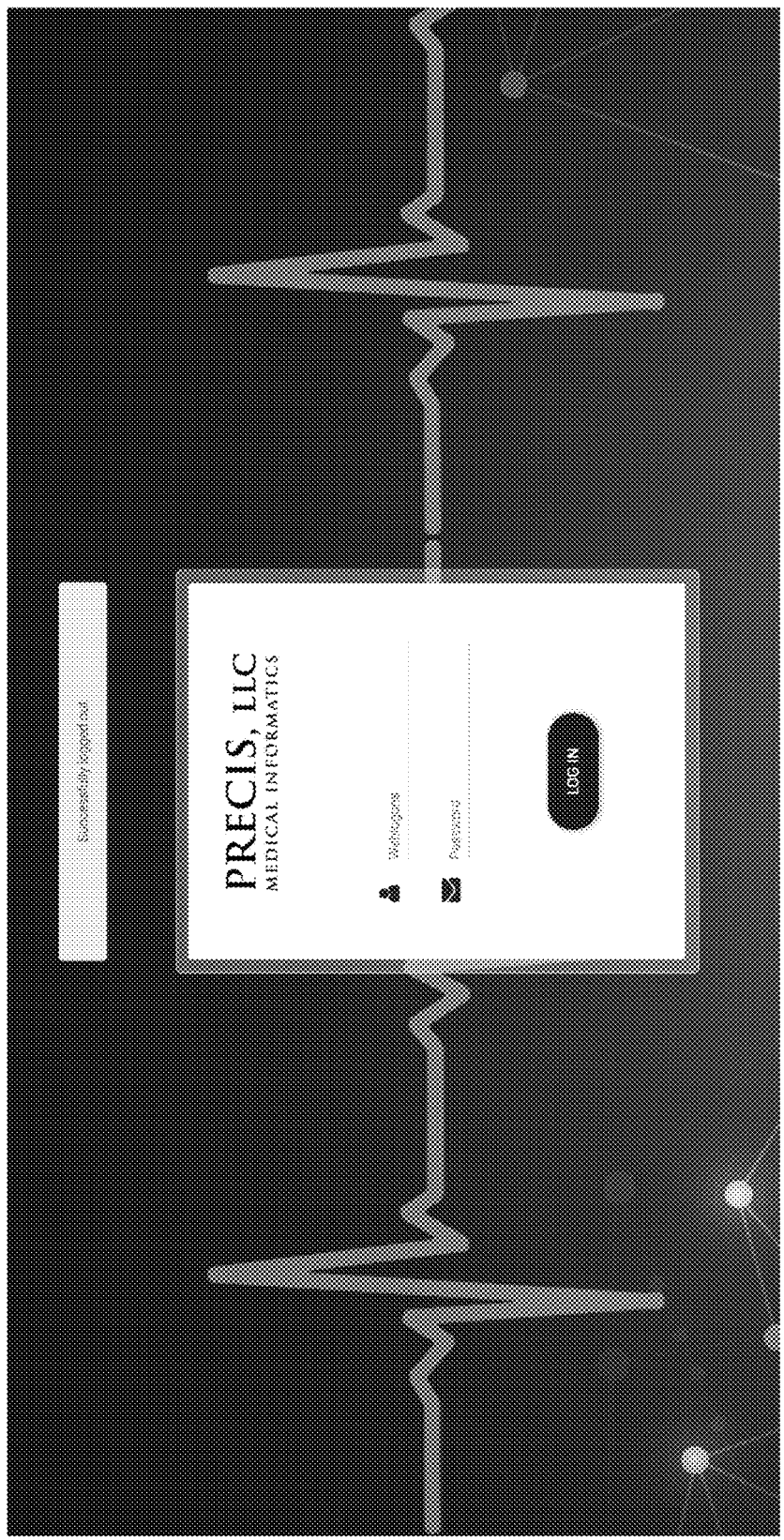

FIG. 15C depicts a non-limiting an example of a Patient Portal Login page 1520 that can provide, for example, a login screen where patients may enter credential information, such as a user name and password.

Figure 15D:
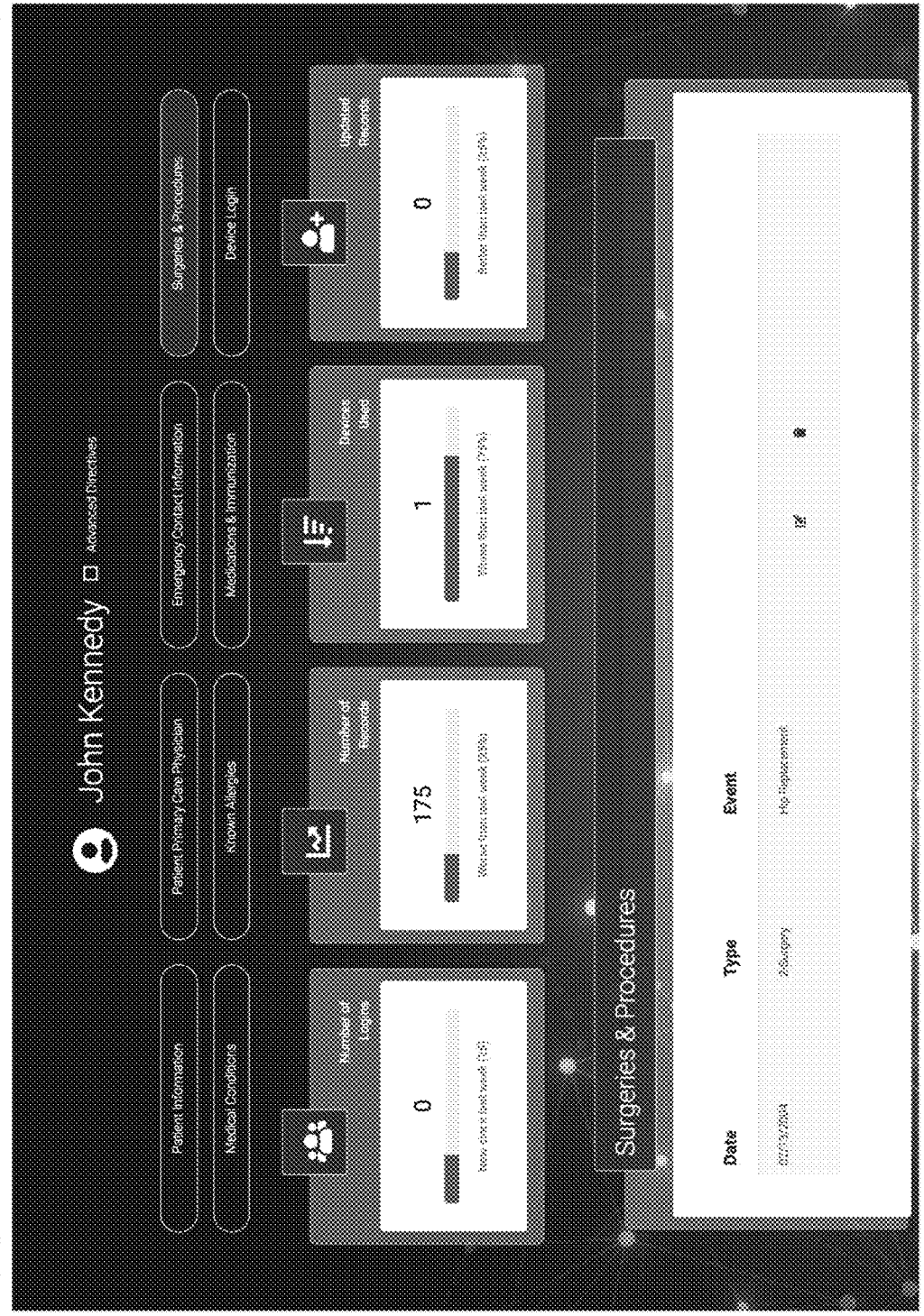

FIG. 15D depicts a non-limiting an example of a Patient Portal Surgeries and Procedures page 1530 that can provide, for example, a historical listing of patient specific surgeries, procedures and related data.

Processing Devices and Processors

In some embodiments, the platforms, systems, media, and methods described herein include processing devices, processors, or use of the same. In further embodiments, the processing device includes one or more hardware central processing units (CPUs) or general purpose graphics processing units (GPUs) that carry out the device's functions. In still further embodiments, the processing device further comprises an operating system configured to perform executable instructions. In some embodiments, the processing device is optionally connected to a computer network. In further embodiments, the processing device is optionally connected to the Internet such that it accesses the World Wide Web. In still further embodiments, the processing device is optionally connected to a cloud computing infrastructure. In other embodiments, the processing device is optionally connected to an intranet. In other embodiments, the processing device is optionally connected to a data storage device.

In accordance with the description herein, suitable processing devices include, by way of non-limiting examples, cloud computing resources, server computers, server clusters, desktop computers, laptop computers, notebook computers, sub-notebook computers, netbook computers, netpad computers, handheld computers, mobile smartphones, and tablet computers.

In some embodiments, the processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the processing device includes a storage or memory device. The storage or memory device is one or more physical apparatuses used to store data or programs on a temporary or permanent basis. In some embodiments, the device is volatile memory and requires power to maintain stored information. In some embodiments, the device is non-volatile memory and retains stored information when the processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, compact disc read-only memories (CD-ROMs), digital versatile discs (DVDs), flash memory devices, magnetic disk drives, magnetic tapes drives, optical disk drives, and cloud computing based storage. In further embodiments, the storage or memory device is a combination of devices such as those disclosed herein.

In some embodiments, the processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display.

In some embodiments, the processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

Referring to FIG. 16, in a particular embodiment, an exemplary processing device 1601 is programmed or otherwise configured to, for example, dynamically load data provider connector modules or request, procure, process, analyze, persist or provide one or more data records. In this embodiment, the processing device 1601 includes a CPU (also "processor" and "computer processor" herein) 1605, which can be a single core or multi core processor, or a plurality of processors for parallel processing. The processing device 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The processing device 1601 can be operatively coupled to a computer network ("network") 1630 with the aid of the communication interface 1620. The network 1630 can be the Internet, an internet or extranet, or an intranet or extranet that is in communication with the Internet. The network 1630 in some cases is a telecommunication or data network. The network 1630 can include one or more computer servers, server clusters or distributed computing resources, providing, for example cloud computing. The network 1630, in some cases with the aid of the device 1601, can implement a peer-to-peer network, which may enable devices coupled to the device 1601 to behave as a client or a server.

Continuing to refer to FIG. 16, the CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. The CPU 1605 can be part of a circuit, such as an integrated circuit. One or more other components of the device 1601 can be included in the circuit. In some cases, the circuit is an application specific integrated circuit (ASIC) or a field programmable gate array (FPGA).

Continuing to refer to FIG. 16, the storage unit 1615 can store files, such as drivers, libraries and saved programs. The storage unit 1615 can store user data, e.g., user preferences and user programs. The processing device 1601 in some cases can include one or more additional data storage units that are external, such as located on a remote server, remote server cluster, network attached storage, or the like, that is in communication through an intranet or the Internet.

Continuing to refer to FIG. 16, methods as described herein can be implemented by way of machine (e.g., computer processor) executable code stored on an electronic storage location of the processing device 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

In some embodiments, the processing device 1601 can include or be in communication with an electronic display 1635. In some embodiments, the electronic display 1635 provides a UI 1640 that depicts various screen such as the examples depicted in FIGS. 14A-14G and 15A-15D.

Non-Transitory Computer Readable Storage Medium

In some embodiments, the platforms, systems, media, and methods disclosed herein include one or more non-transitory computer readable storage media encoded with a program including instructions executable by the operating system of an optionally networked processing device. In further embodiments, a computer readable storage medium is a tangible component of a processing device. In still further embodiments, a computer readable storage medium is optionally removable from a processing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the processing device's CPU, written to perform one or more specified tasks. Computer readable instructions may be implemented as program modules, such as functions, objects, APIs, data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™ and Unity®.

Mobile Application

In some embodiments, a computer program includes a mobile application provided to a mobile processing device. In some embodiments, the mobile application is provided to a mobile processing device at the time it is manufactured. In other embodiments, the mobile application is provided to a mobile processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Software Modules

In some embodiments, the platforms, systems, media, and methods disclosed herein include software, server, or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Data Stores

In some embodiments, the platforms, systems, media, and methods disclosed herein include one or more data stores, or use of the same. In view of the disclosure provided herein, those of skill in the art will recognize that data stores are repositories for persistently storing and managing collections of data. Types of data stores repositories include, for example, databases and simpler store types, or use of the same. Simpler store types include files, emails, and so forth. In some embodiments, a database is a series of bytes that is managed by a DBMS. Many databases are suitable for receiving various types of data, such as medical, patient, weather, maritime, environmental, civil, governmental, or military data. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In some embodiments, a database is web-based. In some embodiments, a database is cloud computing-based. In some embodiments, a database is based on one or more local computer storage devices.

While preferred embodiments of the present disclosure have been shown and described herein, it will be obvious to those skilled in the art that such embodiments are provided by way of example only. Numerous variations, changes, and substitutions will now occur to those skilled in the art without departing from the described system. It should be understood that various alternatives to the embodiments described herein may be employed in practicing the described system.

What is claimed is:

1. A data abstraction system comprising:
   a) a data store comprising one or more data records, the data store defined according to a data format schema, the one or more data records comprising at least one Electronic Health Record (EHR);
   b) one or more processors; and
   c) a computer-readable storage device comprising non-volatile memory, the computer-readable storage device coupled to the one or more processors and having instructions stored thereon which, when executed by the one or more processors, cause the one or more processors to provide a horizontally scalable cloud architecture and perform automated data abstraction operations via the horizontally scalable cloud architecture, the operations comprising:
i) maintaining, on the non-volatile memory, a plurality of definitions of data provider connector modules wherein each definition of a data provider connector module comprises a preferred communication protocol;
ii) retrieving a selected definition of a data provider connector module from the non-volatile memory without accessing or querying a database implementation;
iii) dynamically loading the data provider connector module based on the selected definition, the data provider connector module configured for a data provider endpoint, wherein the data provider endpoint does not interoperate with other data provider endpoints registered with the data abstraction system, the data provider connector module comprising: a sync scheduling definition, an accessor communication protocol client, a data translator module, and a data mapping system;
iv) receiving an instruction, in accordance with the sync scheduling definition, to request a data payload comprising one or more new or updated data records from the data provider endpoint over a network, the one or more new or updated data records defined according to a data records schema specified for the data provider endpoint;
v) procuring, via the accessor communication protocol client, the data payload from the data provider endpoint over the network, wherein the accessor communication protocol client supports communication protocol switching among a plurality of supported protocols, and wherein the accessor communication protocol client processes the data records based on the preferred communication protocol;
vi) processing, by the data translator module, the one or more new or updated data records by performing a set of automated mapping operations to map the data records schema to the data format schema;
vii) retrieving, by the data mapping system, one or more of the data records from the data store;
viii) assigning weighted values to a specified set of fields and attributes for each of the retrieved data records according to the mapped schemas and based on values for corresponding fields and attributes in the one or more new or updated data records;
x) applying, by the data mapping system, an algorithm to evaluate a record match based on a calculated point value sum of the fields within the data record that match against a calculated match likelihood of N number of the matching fields;
x) persisting the one or more new or updated data records to the data store; and
xi) making the one or more data records available via a standardized communication protocol or a user interface.

2. The data abstraction system of claim 1, wherein the data provider connector module is dynamically loaded through reflection or introspection of code.

3. The data abstraction system of claim 1, wherein the data provider connector module further comprises a test connection method.

4. The data abstraction system of claim 1, wherein the accessor communication protocol client connects to the data provider endpoint after authenticating through an authentication service preconfigured at the data provider.

5. The data abstraction system of claim 4, wherein the definition of the data provider connector module comprises credentials, a Uniform Resource Identifier (URI), and an authentication protocol for the authentication service.

6. The data abstraction system of claim 1, wherein the definition of the data provider connector module further comprises custom automated instructions that define the communication protocol and automated mapping operations for the data provider connector module.

7. The data abstraction system of claim 1, wherein the automated mapping operations for the data records schema include custom fields defined by the data mapping system.

8. The data abstraction system of claim 1, wherein the automated data abstraction operations further comprise, before persisting the updated data records, encrypting the updated data records.

9. The data abstraction system of claim 1, wherein the accessor communication protocol client procures the data payload from the data provider endpoint based on a specified technology standard.

10. The data abstraction system of claim 1, wherein the plurality of supported protocols comprises: Fast Healthcare Interoperability Resources (FHIR), and Representational State Transfer (REST), and wherein FHIR is used preferentially and a non-FHIR supported protocol is used where FHIR is not available at the data provider endpoint.

11. The data abstraction system of claim 1, wherein the plurality of supported protocols is defined by the definition of the data provider connector module.

12. The data abstraction system of claim 1, wherein the instruction is received from a time-based job scheduler, and wherein the instruction comprises a software-based trigger.

13. The data abstraction system of claim 1, wherein the automated data abstraction operations comprise:
discarding at least one of the data records based on low measures of the weighted values assigned to the specified set of fields and attributes of the at least one of the data records.

14. The data abstraction system of claim 1, wherein the data abstraction is defined according to the definition of the data provider connector module.

15. The data abstraction system of claim 1, wherein the data store comprises an in-memory database.

16. The data abstraction system of claim 1, wherein the data provider connector module is implemented as a node allocated to the data provider endpoint.

17. The data abstraction system of claim 1, wherein the data store is load balanced, and wherein the data store is replicated through a master/master replication system.

18. The data abstraction system of claim 1, wherein the one or more of the data records are retrieved from the data store based on fuzzy search logic.

19. The data abstraction system of claim 1, comprising a plurality of data provider connector modules dynamically loaded based on respective definitions retrieved from the computer-readable storage device, each of the definitions comprising: a sync scheduling definition, an accessor communication protocol client, a data translator module, and a data mapping system.

20. The data abstraction system of claim 19, wherein each of the data provider connector modules is hosted at a distinct server, server cluster, or cloud node.

21. The data abstraction system of claim 1, further comprising a user device, wherein the user interface is included in a client instantiated on the user device, wherein the user interface is provided at least one of the data records via a FHIR communication protocol implemented Application Programming Interface (API), and wherein a last sync time and a device identifier associated with the user device is persisted for the user interface by the API.

22. The data abstraction system of claim 1, wherein the one or more data records are made available via FHIR coupled with a standardized API.

23. The data abstraction system of claim 1, wherein the data provider endpoint and the data provider connector module support one or more of: Health Level-7 (HL7), International Classification of Diseases 10 (ICD-10), and FHIR.

24. The data abstraction system of claim 1, wherein the at least one EHR comprises at least one Electronic Medical Record (EMR).

25. The data abstraction system of claim 1, wherein the one or more new or updated data records comprise at least one new or updated EHR.

26. The data abstraction system of claim 25, wherein the at least one new or updated EHR comprises at least one new or updated EMR.

27. The data abstraction system of claim 1, wherein the data abstraction is defined for the data provider endpoint such that the data provider endpoint does not interoperate with other data provider endpoints registered with the data abstraction system.

28. The data abstraction system of claim 1, wherein the non-volatile memory comprises a disk.

29. A computer-implemented data abstraction method provided via a horizontally scalable cloud architecture, the method comprising:
   a) maintaining a data store comprising one or more data records, the data store defined according to a data format schema, the one or more data records comprising at least one Electronic Health Record (EHR);
   b) maintaining, on a computer-readable storage device comprising non-volatile memory non-volatile memory, a plurality of definitions of data provider connector modules wherein each definition of a data provider connector module comprises a preferred communication protocol;
   c) retrieving a selected definition of a data provider connector module from the non-volatile memory without accessing or querying a database implementation;
   d) dynamically loading the data provider connector module based on the selected definition, the data provider connector module configured for a data provider endpoint, wherein the data provider endpoint does not interoperate with other data provider endpoints registered with the data abstraction system, the data provider connector module comprising: a sync scheduling definition, an accessor communication protocol client, a data translator module, and a data mapping system;
   e) receiving an instruction, in accordance with the sync scheduling definition, to request a data payload comprising one or more new or updated data records from the data provider endpoint over a network, the one or more new or updated data records defined according to a data records schema specified for the data provider endpoint;
   f) procuring, via the accessor communication protocol client, the data payload from the data provider endpoint over the network, wherein the accessor communication protocol client supports communication protocol switching among a plurality of supported protocols, and wherein the accessor communication protocol client processes the data records based on the preferred communication protocol;
   g) processing, by the data translator module, the one or more new or updated data records by performing a set of automated mapping operations to map the data records schema to the data format schema;
   h) retrieving, by the data mapping system, one or more of the data records from the data store;
   i) assigning weighted values to a specified set of fields and attributes for each of the retrieved data records according to the mapped schemas and based on values for corresponding fields and attributes in the one or more new or updated data records;
   j) applying, by the data mapping system, an algorithm to evaluate a record match based on a calculated point value sum of the fields within the data record that match against a calculated match likelihood of N number of the matching fields;
   k) persisting the one or more new or updated data records to the data store; and
   l) making the one or more data records available via a standardized communication protocol or a user interface.

30. A non-transitory computer-readable storage media encoded with a computer program including instructions executable by one or more processors to provide a horizontally scalable cloud architecture and perform automated data abstraction operations via the horizontally scalable cloud architecture, the operations comprising:
   a) maintaining a data store comprising one or more data records, the data store defined according to a data format schema, the one or more data records comprising at least one Electronic Health Record (DAR);
   b) maintaining, on a computer-readable storage device comprising non-volatile memory non-volatile memory, a plurality of definitions of data provider connector modules wherein each definition of a data provider connector module comprises a preferred communication protocol;
   c) retrieving a selected definition of a data provider connector module from the non-volatile memory without accessing or querying a database implementation;
   d) dynamically loading the data provider connector module based on the selected definition, the data provider connector module configured for a data provider endpoint, wherein the data provider endpoint does not interoperate with other data provider endpoints registered with the data abstraction system, the data provider connector module comprising: a sync scheduling definition, an accessor communication protocol client, a data translator module, and a data mapping system;
   e) receiving an instruction, in accordance with the sync scheduling definition, to request a data payload comprising one or more new or updated data records from the data provider endpoint over a network, the one or more new or updated data records defined according to a data records schema specified for the data provider endpoint;
   f) procuring, via the accessor communication protocol client, the data payload from the data provider endpoint over the network, wherein the accessor communication protocol client supports communication protocol switching among a plurality of supported protocols, and wherein the accessor communication protocol client processes the data records based on the preferred communication protocol;

g) processing, by the data translator module, the one or more new or updated data records by performing a set of automated mapping operations to map the data records schema to the data format schema;

h) retrieving, by the data mapping system, one or more of the data records from the data store;

i) assigning weighted values to a specified set of fields and attributes for each of the retrieved data records according to the mapped schemas and based on values for corresponding fields and attributes in the one or more new or updated data records;

j) applying, by the data mapping system, an algorithm to evaluate a record match based on a calculated point value sum of the fields within the data record that match against a calculated match likelihood of N number of the matching fields;

k) persisting the one or more new or updated data records to the data store; and l) making the one or more data records available via a standardized communication protocol or a user interface.

* * * * *